US008522776B2

(12) United States Patent
Wright et al.

(10) Patent No.: US 8,522,776 B2
(45) Date of Patent: Sep. 3, 2013

(54) INHALER

(75) Inventors: Matthew Paul Wright, Newmarket (GB); Mike Sheldon, Cambridge (GB); Matthew Sarkar, Cambridge (GB); Ivan Milivojevic, Cambridge (GB); Roger Clarke, Histon (GB); Emma Lesley Williamson, Cambridge (GB)

(73) Assignee: Vectura Delivery Devices Limited (GB)

( * ) Notice: Subject to any disclaimer, the term of this patent is extended or adjusted under 35 U.S.C. 154(b) by 967 days.

(21) Appl. No.: 12/456,168

(22) Filed: Jun. 12, 2009

(65) Prior Publication Data

US 2010/0192949 A1      Aug. 5, 2010

(30) Foreign Application Priority Data

Jan. 30, 2009   (GB) .................................. 0901520.7

(51) Int. Cl.
*A61M 5/00*           (2006.01)
(52) U.S. Cl.
USPC ................................ 128/203.15; 128/203.21
(58) Field of Classification Search
USPC ............................ 128/203.12, 203.21, 203.15
See application file for complete search history.

(56) References Cited

U.S. PATENT DOCUMENTS

| 4,627,432 | A | * | 12/1986 | Newell et al. | ............ | 128/203.15 |
| 4,678,106 | A | * | 7/1987 | Newell et al. | ................. | 222/162 |
| 4,811,731 | A | * | 3/1989 | Newell et al. | ............ | 128/203.15 |
| 5,035,237 | A | * | 7/1991 | Newell et al. | ............ | 128/203.15 |
| 2011/0120463 | A1 | | 5/2011 | Esteve et al. | | |

FOREIGN PATENT DOCUMENTS

| EP | 129985 | A | * | 1/1985 |
| EP | 129985 | A1 | * | 1/1985 |
| EP | 0491426 | A1 | | 6/1992 |
| GB | 1472650 | A | | 5/1977 |
| GB | 2246299 | A | * | 1/1992 |
| GB | 2264237 | A | * | 8/1993 |
| GB | 2407042 | A | * | 4/2005 |
| GB | 2420982 | A | | 6/2006 |
| GB | 2439204 | A | * | 12/2007 |
| JP | 05200100 | A | * | 8/1993 |
| WO | WO 2007/098870 | A1 | | 9/2007 |
| WO | WO 2009/004465 | A1 | | 8/2009 |

OTHER PUBLICATIONS

Search Report from the UK Patent Office, mailed on Oct. 5, 2009, issued in connection with corresponding GB Application No. GB0909606.6.

\* cited by examiner

*Primary Examiner* — Stephen Crow
(74) *Attorney, Agent, or Firm* — Davidson, Davidson & Kappel, LLC

(57) ABSTRACT

An inhalation device comprising a base having a slot for insertion of a single blister containing a dose of medicament to be inhaled into the base is disclosed. The inhaler has a mouthpiece pivotally mounted to the base which carries a blister piercing element operable to pierce a blister received in said slot when the mouthpiece is pivoted relative to the base. When a user inhales on the mouthpiece, the dose is entrained in an airflow and flows out of the blister through the mouthpiece and into the user's airway.

61 Claims, 24 Drawing Sheets

INHALER

This application claims priority to United Kingdom Patent Application No. GB 0901520.7, filed Jan. 30, 2009, the disclosures of which are hereby incorporated by reference in their entirety.

FIELD OF THE INVENTION

The present invention relates to an inhalation device for oral or nasal delivery of medicament in powdered form and more specifically to a unit-dose inhaler which may contain or be loaded with a single blister that has a breachable lid or base and which contains a single dose of medicament for inhalation by a user of the device.

BACKGROUND

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs thereby avoiding the need for hypodermic injections.

It is common for dry powder formulations to be pre-packaged in individual doses, usually in the form of capsules or blisters each of which contain a single dose of the powder that has been accurately and consistently measured. A blister is generally cold formed from a ductile foil laminate or a plastics material and includes a puncturable or peelable lid which is heat-sealed around the periphery of the blister during manufacture and after introduction of the dose into the blister. A foil blister is preferred over a polymer blister or gelatine capsule as each dose is protected from the ingress of water and penetration of gases such as oxygen in addition to being shielded from light and UV radiation all of which can have a detrimental effect on the delivery characteristics of the inhaler if a dose becomes exposed to them. Therefore, a blister offers excellent environmental protection to each individual drug dose.

It is known to provide an inhaler that is capable of holding a number of doses to enable it to be used repeatedly over a period of time without the requirement to open and/or insert a blister into the device each time it is used. Such a device is known from the Applicant's own earlier international application which has been published as WO 2005/037353 A1.

However, it is also desirable to provide a simple, low-cost unit-dose device that receives only one blister at a time. Once the dose contained in a blister has been inhaled, the blister is removed from the device and discarded by the patient. A fresh blister is then inserted into the device for a subsequent dose. This avoids the need for a strip indexing mechanism and so greatly simplifies the construction and operation of the device as well as reducing its overall dimensions.

A re-usable, unit-dose, passive dry powder inhaler for the delivery of medicinal products is known. The dose is pre-metered and contained in a foil blister to ensure the highest possible degree of protection for the drug together with reproducible dosing. The individual blister may be provided with a tab to enable a user to grasp it easily without damaging the dose containing cavity or blister bowl and to facilitate its insertion into the device and its subsequent removal therefrom after inhalation. Actuation of the device causes a piercing element to breach or rupture an inserted blister bowl so that when the patient inhales through the mouthpiece of the device, air is drawn through the blister to entrain the dose contained therein which is then carried out of the blister through the device and via the patient's airway down into the lungs.

DESCRIPTION

The present invention seeks to provide a unit-dose dry powder inhalation device that represents an improvement over known unit-dose type inhalation devices and which is easier to use and inexpensive to produce.

Although the present invention refers to embodiments in which the device is intended to be loaded with a blister immediately prior to use, other 'pre-loadable' device embodiments are also described. By 'preloadable' is meant a device which is designed so that a blister may be inserted into the device which is then maintained in a pre-punctured state ready for use at a later time so that the patient has immediate access to a dose whenever required and does not have to load the device with a blister immediately prior to inhalation. With many existing devices, it is difficult or impossible to pre-load them without inadvertent piercing of the blister occurring during transport and prior to actual inhalation of the dose, usually because the device must be primed or opened in some way to enable the blister to be inserted, movement back into its original state then causing the blister to be pierced. However, in a primed state the device is relatively unstable and premature piercing can easily occur by accident. Furthermore, if the blister is provided with a tab to enable a user to grasp it more easily, the tab may protrude from the device when the blister bowl is in a piercing-ready position which also makes it harder to carry comfortably and may also preclude the attachment of a cap or cover over the device when it is not being used because the blister tab is in the way.

To ensure that a powdered medicament is delivered with an accurately controlled range of particle sizes in order that they are absorbed effectively in the lung, it is necessary to deagglomerate the particles as they flow through the device prior to entry into the patient's airway. To achieve this, the Applicant's co-owned and co-pending European patent application no. 08100886.4 describes an inhaler which includes an aerosolising device having a generally cylindrical chamber and inlet and outlet ports at opposite ends of the chamber for the flow of drug laden air through the chamber, entering axially at the inlet port and exiting at the outlet port. The inhaler also has tangential bypass air inlets for the flow of clean, non-drug laden air into the chamber which forms a cyclone in the chamber that interacts with the drug laden air flowing between the inlet and outlet ports. As the bypass air forms a cyclone within the device the drug laden air flow is caused to rotate and follow at least a part helical path towards the outlet port due to the effect of the cyclone upon it. This interaction of the vortex formed from the bypass air spinning around chamber on the drug laden air flowing into the chamber in an axial direction results in an improvement in the performance of the inhaler as the drug laden air is accelerated as it flows through the chamber and experiences increased shear forces and differential velocities which further deagglomerate the particles and improve the fine particle fraction of the emitted dose.

Although not essential to the unit-dose inhalation device of the present invention, the concepts described in the earlier application referred to above may also be applied to any embodiment of unit-dose inhaler of the present application to provide the associated advantages of increased deagglomeration and fine particle fraction of the delivered dose in a unit-dose inhaler. A generalised embodiment of the device disclosed in EP08100886.4 is described in more detail below, with reference to FIGS. 1A and 1B of the accompanying drawings, prior to describing specific embodiments of a unit dose inhaler according to the present invention and which incorporate a bypass air cyclone of the type described in this previous application.

According to the present invention, there is provided an inhaler comprising a housing having a mouthpiece through which a user may inhale a dose of medicament and a blister support member having a slot to receive a dose containing blister, the housing and the blister support member being pivotable relative to each other between a first position for insertion of a blister into said slot and, a second, pierced position, in which a blister piercing element carried by the housing pierces an inserted blister so that when a user inhales on the mouthpiece, the dose is entrained in an airflow and flows out of the blister through the mouthpiece and into the user's airway.

In one embodiment, the blister support member is pivotally mounted within, and extends from, the housing to enable a user to pivot the blister support member relative to the housing into said second, pierced position so that a blister inserted into the slot and supported by the blister support member is pierced by said blister piercing element.

The blister support member may include a lever portion that extends into a cut-out section formed in a wall of the housing and which fills only a portion of the cut-out section such that the housing and the lever portion together define a recess therebetween.

Preferably, the slot is located such that a blister tab of a blister received in the blister support member protrudes from said slot into said recess. In particular, the slot may be configured such that a blister tab extending into said recess is spaced from the housing and from the blister support member when the blister support member is in its first position.

Advantageously, the blister support member and the housing is configured such that, when the blister support member is rotated into its second, pierced position, a blister tab protruding from the aperture into the recess lies substantially against the housing and/or is in a less accessible or clearly visible position than when the blister support member is in its first position. As the blister tab is less accessible and/or visible, it less likely that the user will attempt to remove or pull the blister out of the device when the blister support member is in its pierced position.

In one embodiment, the housing has opposite end walls and the cut-away section is formed in one of said end walls, the lever portion extending into said cut-away section being shaped so as to partially resemble the non-cut-away section of said opposite end wall.

Preferably, the housing has a lower end remote from the mouthpiece, said lower end comprising a laterally protruding shoulder to support a protective cap located over the housing. Ideally, the lever portion also includes a shoulder that forms an extension of the shoulder on the housing when the lever portion is in its first position, such that a cap is supported by both the shoulder on the housing and the shoulder extension on the lever portion.

In a preferred embodiment, the protective cap extends over the recess formed by said cut-away section of the housing and said lever portion without interfering with a blister tab of a blister received in the housing and extending into said recess.

The lever portion may be configured such that, if a cap is placed over the housing with the blister support member in its second, pierced position, the cap contacts the shoulder on the lever portion so that further movement of the cap onto the housing causes the cap to rotate the lever portion back into its first position.

In a preferred embodiment, arcuate guide surfaces are formed on the housing, the lever portion having a cooperating guide member that slides along the guide surfaces to guide movement of the lever portion between its first and second positions.

The blister support member may include a resilient arm having a tongue at its free end that is biased against the inner surface of the housing, the housing having detents positioned such that said tongue locates in respective detents when said blister support member is in its first and second positions.

The inhaler may have a base member that closes a lower end of the housing remote from the mouthpiece, said base member having a wall to support the housing upright on a flat surface.

In one embodiment, the lever portion has an underside that forms a continuation of said wall of the base member when said lever portion is in its non-pierced position such that, when the inhaler is placed upright on a flat surface, the inhaler is supported by said wall and the underside of the lever portion.

The blister support member may contact the base member in its first position and prevent the blister support member from rotating beyond said first position in a direction away from its second position.

In one embodiment, the base member comprises a resilient arm that extends upwardly within the housing from the wall of the base member, the free end of said arm having a tongue that engages in an opening in the housing to attach the base to the housing.

Preferably, the tongue protrudes through the opening beyond the outer surface of the housing to contact a cap located over the housing.

According to another preferred embodiment, the housing is pivotable by a user relative to the blister support member between said first and second positions.

In any embodiment of inhaler according to the present invention, the blister support member may comprise a seat to support a blister that has been inserted through the slot in its first position. The housing of the inhalers according to the invention may also comprise a substantially cylindrical chamber having an inlet at one end for the flow of drug laden air into the chamber from a pierced blister and an outlet at its opposite end for the flow of drug laden air out of the mouthpiece and into a patient's airway.

Preferably, the chamber has a longitudinal axis that extends between the inlet and the outlet and the substantially cylindrical chamber has at least one bypass air inlet for the flow of clean air into the cyclone chamber to interact with the drug laden air flowing between the inlet and the outlet. The bypass air inlet(s) may meet the chamber at a tangent so that a cyclonic air flow is generated from clean air that interacts with the drug laden air flow.

In a preferred embodiment, the chamber and bypass air inlets comprise an insert located within the housing.

Preferably, the housing comprises a pair of spaced side walls with the insert being located between the side walls, the side walls extending laterally beyond the ends of the bypass air inlets.

In one embodiment, the housing has a home or storage position in which the housing is located in a lowered position against the blister support member and the blister piercing element is in a position in which a blister located in the blister support member is pierced by the piercing elements. The housing may then also have a primed position in which it is pivoted relative to the blister support member out of its home or storage position into a raised position in which the housing is angled relative to the blister support member and in which the blister piercing element is moved out of a blister pierced position to enable a blister to be inserted into the blister support member through said slot and subsequently removed therefrom.

In one embodiment, the longitudinal axis of the chamber is substantially at right-angles to the direction of insertion of a blister into the blister support member, when the blister support member is in its home or storage position.

A cap may be positionable over the housing and the blister support member only when the housing is in its home or storage position.

In another embodiment, the housing has a home or storage position in which the housing is raised relative to the blister support member and the direction of insertion of a blister into the slot is angled relative to the longitudinal axis of the chamber. The housing may then have a pierced position in which it is pivoted out of its home or storage position into a lowered angled position against the blister support member in which the blister piercing elements assume a blister pierced position to pierce a blister inserted into the blister support member at an angle through the slot.

In this embodiment, the longitudinal axis of the chamber is substantially at right-angles to the direction of insertion of a blister into the blister support member, when the housing is in its lowered blister pierced position.

In some preferred embodiments, the blister support member is configured so as to support a blister such that the plane of a blister surrounding the blister bowl lies at an acute angle relative to the longitudinal axis of the chamber when the housing is in its home position prior to pivotal movement of the housing to lower it onto the blister support member to pierce said blister.

Preferably, the longitudinal axis of the chamber lies substantially at right-angles to the plane of a lid of a blister after the housing has been pivoted out of its home position into its lowered position to pierce said blister.

In preferred embodiments, the blister support member has a lower supporting surface to stand the blister support member, together with the housing, upright on a level surface when not in use and the longitudinal axis of the chamber may lie substantially at right-angles to the plane of the lower supporting surface when lo the housing is in a first position prior to pivotal movement of the housing relative to the blister support member to pierce said blister.

Preferably, the blister seat comprises a blister support surface to support the periphery of a blister surrounding a blister bowl. Ideally, the blister support surface is located below a surrounding wall such that the edges of a blister located on the support surface are supported between the support surface and the surrounding wall. In one embodiment, the blister support surface has a generally U-shaped cut out to receive a blister bowl and an arcuately shaped cantilever arm extends into the cut out from the base of the U-shape. The cantilever can have an enlarged head with a blister bowl engaging lip, the cantilever arm resiliently deforming to allow a blister bowl to ride over the head and locate within the arcuately shaped cantilever arm to retain the blister within the device.

In some embodiments, the blister support member has a tab receiving recess formed in a side wall of the blister support member to receive a folded blister tab of a pre-loaded blister.

In one embodiment, wherein the blister support member has convex shaped support surfaces that cooperate with corresponding concave shaped support surfaces on the housing when the housing is rotated relative to the blister support member.

In preferred embodiments, the slot is formed in a depression in the blister support member so that a blister tab extending from the slot does not protrude beyond the walls of the device.

The inhalation device according to the embodiments of the invention may comprise a cap positionable such that it substantially covers the housing and the blister support member after a blister has been inserted into the slot and whilst the housing is in its first position, the cap being positionable without interfering with a blister tab extending from said slot.

In some embodiments, an opening is preferably formed between the housing and the blister support member to enable a user to see the blister piercing element and a blister inserted into the slot in the blister support member.

An inhalation device according to the embodiments of the invention may also comprise a dose containing blister having a tab such that, when the blister is inserted into the slot, the tab protrudes from the slot and facilitates the removal of the blister from the slot after inhalation.

In some embodiments, the tab is foldable relative to the remaining portion of the blister received in the slot such that the tab lies substantially flush against the base when the blister is received in the slot. The base may comprise a recess to locate a folded tab therein.

Preferably, the base and the cap are configured so that the cap extends over and covers the folded tab.

According to the invention, there is also provided a method of preloading an inhalation device ready for later use, said device comprising a blister support member having a slot, a housing having a mouthpiece and a cap that covers the housing and the blister support member when the device is not in use, the blister support member and the housing being pivotable relative to each other, after removal of the cap, between a first position for insertion of a blister into said slot and, a second, pierced position, in which a blister piercing element carried by the housing pierces an inserted blister, the method including the step of removing the cap, inserting a dose containing blister into the slot when the mouthpiece is in its first position and subsequently replacing the cap such that the cap substantially covers the housing and the blister support member whilst the mouthpiece remains in its storage position and with the dose containing blister received in the slot.

In one embodiment, the blister has a tab, the tab protruding from the slot when the blister is inserted therein to facilitate the removal of the blister from the slot after inhalation, and the method includes the step of folding the tab relative to the remaining portion of the blister received in the slot such that it lies substantially flush against the base. The base may include a recess to receive the blister tab of a blister received in said slot and the method may include the step of folding the tab into the recess in the base prior to placing the cover over the housing and the blister support member.

According to another aspect of the invention, there is provided a blister piercing element for a dry powder inhalation device comprising a metal plate having a plurality of peripheral blister piercing blades bent out of the plane of the plate along fold lines to form drug flow openings through the plate, wherein each blade points away from each of the other peripheral piercing blades and the fold lines of each peripheral piercing blade lies substantially at 90 degrees to the fold line of each of the remaining peripheral piercing blades.

In one embodiment, there are four peripheral piercing blades.

The blister piercing element may also comprise a central piercing blade surrounded by the peripheral piercing blades.

Ideally, the fold line of the central piercing blade extends at an angle relative to the fold lines of each of the four peripheral piercing blades. In one embodiment the fold line of the central piercing blade is angled at 45 degrees to the fold lines of each of the four peripheral piercing blades.

In one embodiment of blister piercing element, arms depend outwardly from the plane of the plate at an angle and tabs extend from the ends of the arms in a plane parallel to the plane of the plate, the tabs having holes therein to facilitate the attachment of the piercing element to an inhalation device.

BRIEF DESCRIPTION OF THE DRAWINGS

Embodiments of the present invention will now be described, by way of example only, and with reference to FIGS. 2A to 20 of the accompanying drawings, in which.

DETAILED DESCRIPTION

Figure 1A:
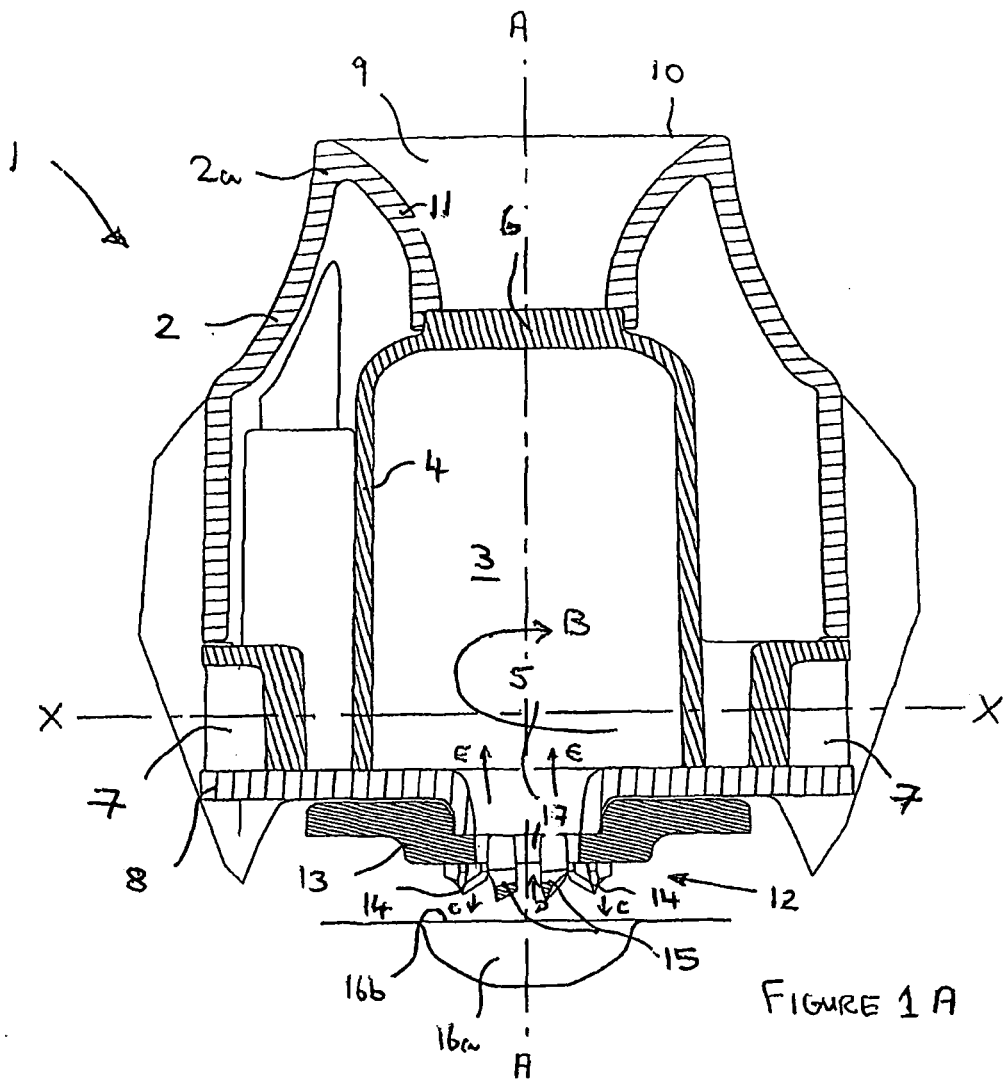
FIG. 1A is a cross-sectional side view of a portion of a generalised inhalation device having a bypass air cyclone, as described and illustrated in the Applicant's earlier co-pending application referred to above.

Referring now to FIG. 1A, there is shown a portion of an inhalation device 1, as described and illustrated in the Applicant's own earlier co-pending application, and in which the bypass air flow is used to assist in the deagglomeration of the drug dose. With reference to FIG. 1A, the device has a housing 2, having a mouthpiece 2a, defining an internal chamber 3 having a chamber wall 4, a drug laden air inlet port 5, an outlet port 6 and bypass air inlets 7. A cross-sectional view taken along the line X-X in FIG. 1A is also shown in FIG. 1B.

The device 1 includes a cyclone chamber closure plate 8 extending across a lower end of the mouthpiece 2 that closes the chamber 3. The drug laden air inlet port 5 is formed in, and extends through, the cyclone closure plate 8 and is coaxial with the longitudinal axis (A-A in FIG. 1A) of the chamber 3.

Although the closure plate 8 can be formed integrally with the housing 2, it is preferably formed as a separate component that is attached to the housing 2 or to the end of the chamber 3 during assembly.

Figure 1B:
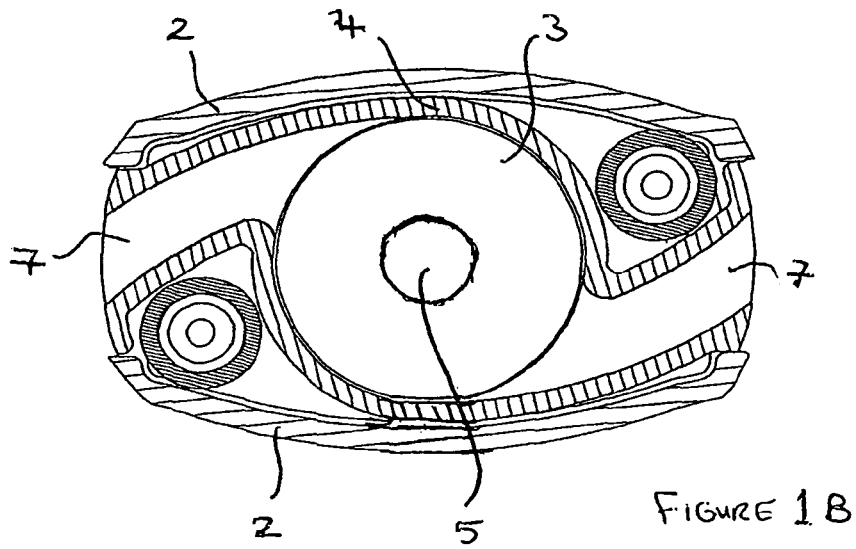
FIG. 1B is a cross-section along the line X-X of the device shown in FIG. 1.

As shown in FIG. 1B, the bypass or clean, non-drug laden air inlets 7 are preferably tangentially oriented arcuately shaped channels formed in the sides of the housing 2 and the closure plate 8 forms the lowermost wall and encloses the lower end of the chamber 3 (apart from the drug laden air inlet port 5), but also forms the lower surface of the channels 7 so that the channels 7 are open only at each of their ends. Although two channels 7 are shown in FIGS. 1A and 1B, it will be appreciated that one channel 7 is also sufficient to produce the desired cyclonic effect.

As the bypass air inlets 7 are arranged tangentially, or so as to direct the bypass air in a substantially tangential direction into the chamber 3, the clean air flowing through these inlets 7 into the chamber 3 is forced to spin around the chamber 3 so as to form a cyclone or vortex (as indicated by arrow "B" in FIG. 1A).

The outlet port 6 may be in the form of a mesh extending across the end of the chamber 3 through which the entrained drug may flow out of the chamber 3 into the patient's airway. Preferably, the mouthpiece 2a incorporates a flow diffuser 9 that extends beyond the outlet port 6 and has a cross-sectional area that gradually increases towards the top edge 10 of the mouthpiece 2a. The wall 11 of the diffuser 9 is curved in shape.

A piercing device 12 is disposed beneath the chamber 3 on the opposite side of the closure plate 8 and may extend from and/or be connected to the closure plate 8. The piercing device 12 comprises a piercing head 13 having piercing elements 14, 15 depending therefrom. The blister piercing elements 14, 15 are configured to puncture the lid 16b of a blister bowl 16a so that, when a patient inhales through the mouthpiece 2, clean air enters the blister bowl 16a through the air inlet flow passages formed by blister piercing elements 14 (in the direction of arrow "C" in FIG. 1A) and entrains the dose contained in the blister bowl 16a. The drug laden air then flows out of the blister 16a through a central drug laden air outlet passage 17 (in the direction of arrow "D"). The drug laden air outlet passage 17 is connected to the drug laden air inlet port 5 of the chamber 3 so that it flows in an axial direction into the chamber 3 (in the direction indicated by arrow "E"). At the same time, clean bypass air enters the chamber 3 through the tangential bypass air inlets 7 and spins around the chamber 3 (in the direction of arrow "B") forming a vortex or cyclone.

Figure 2A:
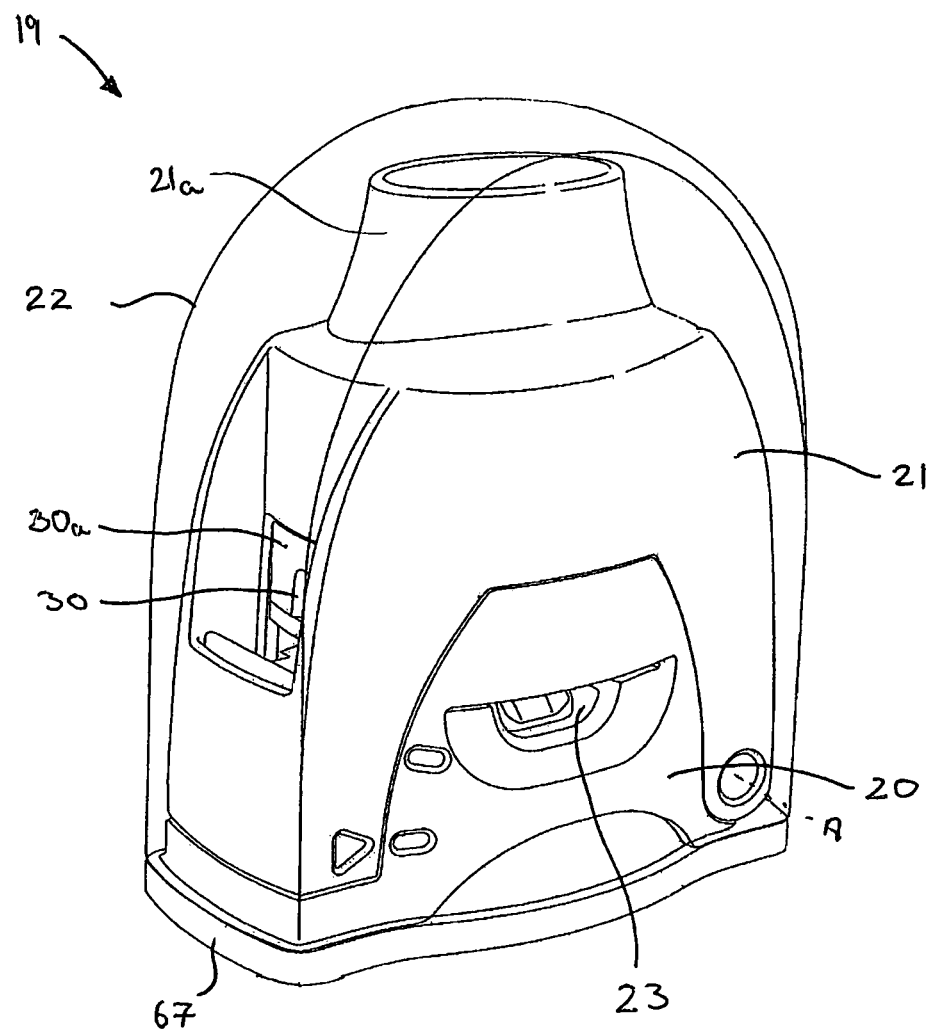
FIG. 2A is a perspective view of a first embodiment of unit-dose inhalation device of the present invention with the housing in a storage or home position on the blister support member and with a cap in place over the housing and blister support member.

Turning now to FIGS. 2A to 2D, there is shown a first embodiment of a unit-dose dry powder inhaler 19 according to the present invention which generally comprises a blister support member 20, a housing 21, having a mouthpiece 21a, pivotally attached to the base and a cap 22 (which may be transparent, as shown in FIG. 2A) that extends over the housing 21 and the blister support member 20. In FIG. 2A, the device is shown in its storage state in which the housing 21 is in its 'home' or storage position and in which the cap 22 covers the housing 21 and blister support member 20 to protect it and to prevent ingress of dirt into the mouthpiece 21a and those parts of the mouthpiece 21a which are inserted into the patient's mouth during inhalation. In this state, with the housing 21 against the blister support member 20, the device is in a stable condition because the housing 21 can only pivot away from the blister support member 20 into an unstable primed position by rotating the housing 21 away from the blister support member 20.

Figure 2B:
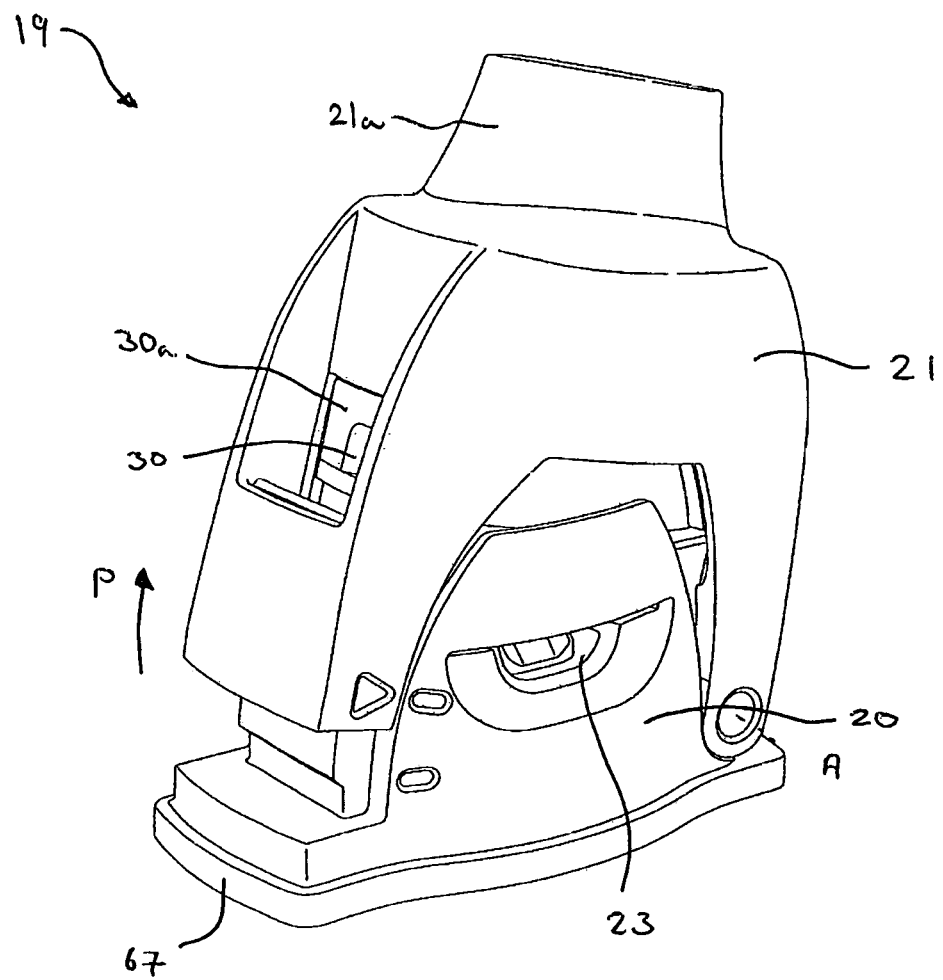
FIG. 2B is a perspective view of the device shown in FIG. 2A but with the cap removed and the housing pivoted out of its home or storage position into its primed position ready for insertion of a blister to be pierced.

FIG. 2B shows the device 19 in its primed state after the cap 22 has been removed and the housing 21 has been pivoted out of its home position (in the direction of arrow "P" about axis "A" in FIG. 2B) ready for insertion of a blister to be punctured through a slot 23 in the side wall of the blister support member 20. It will be appreciated that, in this state, the device is in a relatively unstable condition because it is easy for the housing 21 to be pushed back into its home position in which the housing 21 is against the blister support member when, for example, the device is being carried in a pocket or bag. Therefore, the device described with reference to this embodiment is not intended to be carried in this state but is designed so that a user inserts a blister into the device at the time a dose is to be inhaled, i.e. immediately prior to piercing.

Figure 2C:
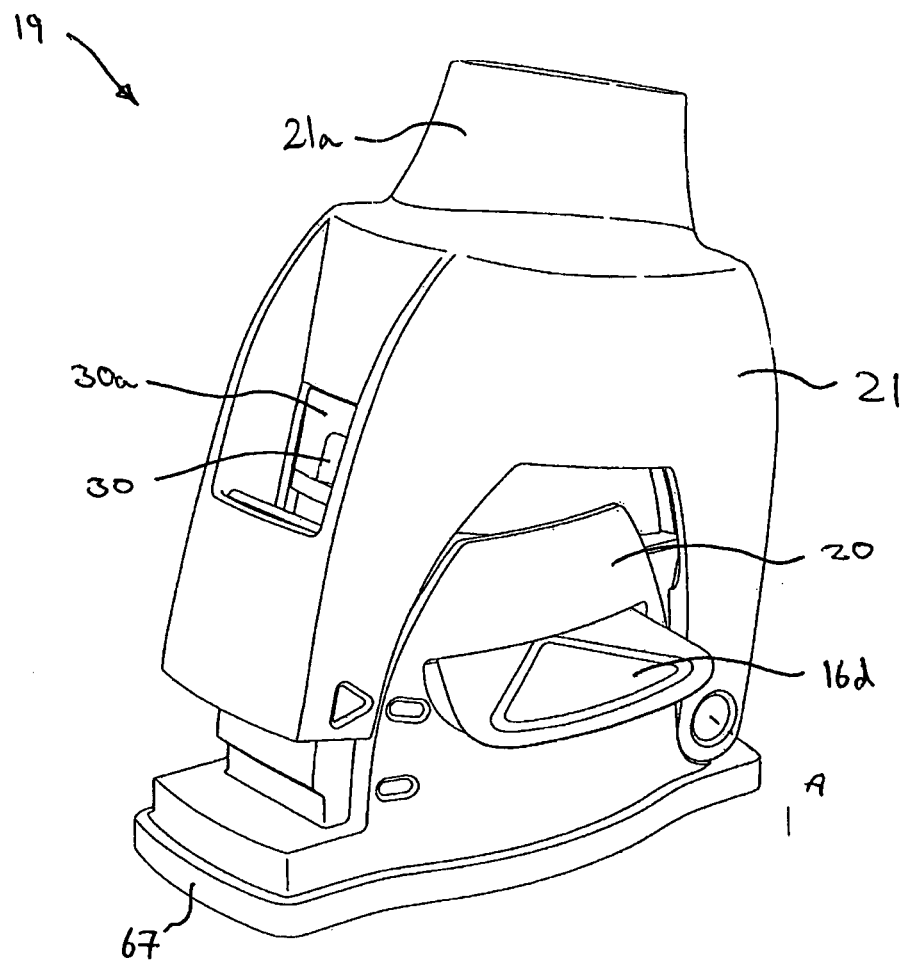
FIG. 2C is the same view as FIG. 2B but following insertion of a blister to be pierced through the slot in the side of the blister support member.

FIG. 2C shows the device as shown in FIG. 2B after a blister has been inserted through the slot 23 in the side of the device 19 and in which a tab 16d, extending from the blister, is visible protruding from the side of the device 19. The tab facilitates the insertion of the blister into the device, and its removal therefrom, as it enables a user to grasp the blister between their fingers placed on either side of the blister tab, without contacting or damaging the blister bowl containing the medicament dose.

Figure 2D:
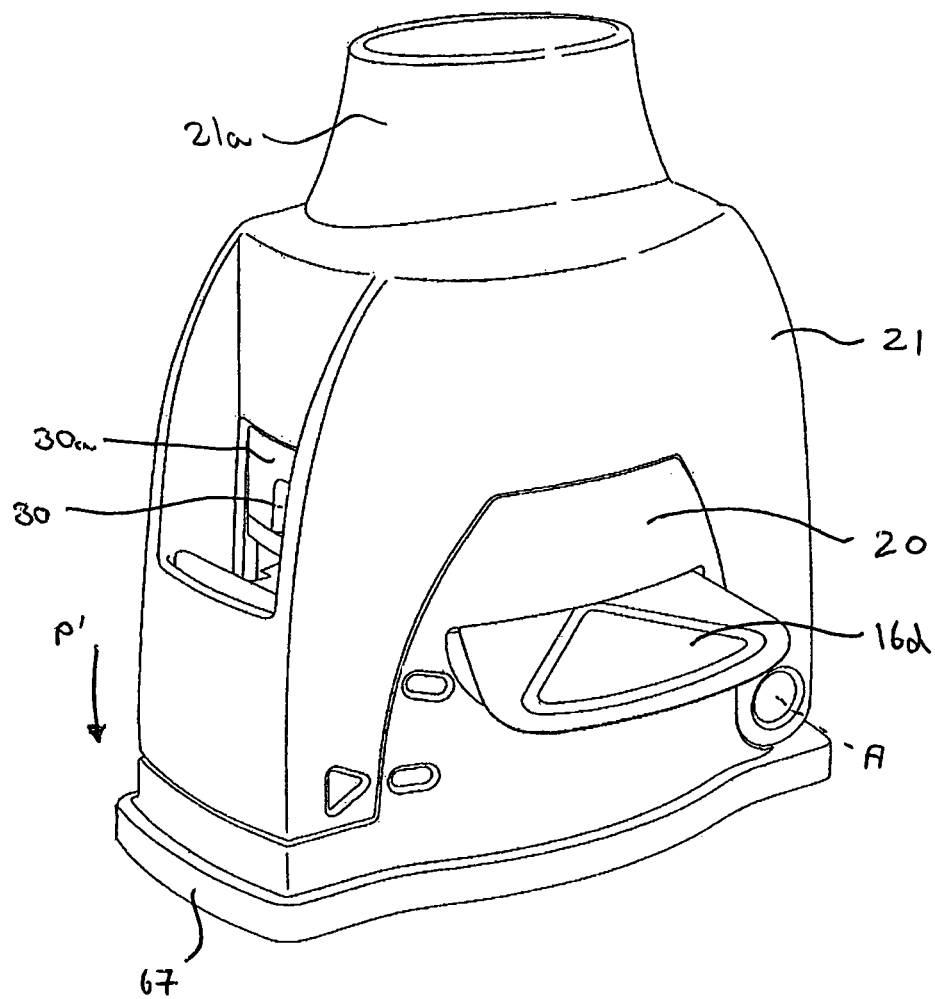
FIG. 2D is a perspective view of the device shown in FIGS. 2A and 2B after the housing has been pivoted back into its home position from its primed position shown in FIG. 2B to pierce an inserted blister.

FIG. 2D shows the device 19 after the housing 21 has been rotated back into its home position in the direction of arrow P' from its position shown in FIG. 2B following insertion of a blister through the slot 23. In this position, the blister has been pierced and the device is ready for a patient to inhale through the mouthpiece 21a.

It will be appreciated that, in this first embodiment, it is only possible to put the cap 22 over the housing 21 and blister support member 20 when the housing 21 is in it home position and no blister is located in the device, as shown in FIG. 2A, because the protruding blister tab would interfere with the cap 22 when the cap is passed over the blister support member 22.

Figure 3A:
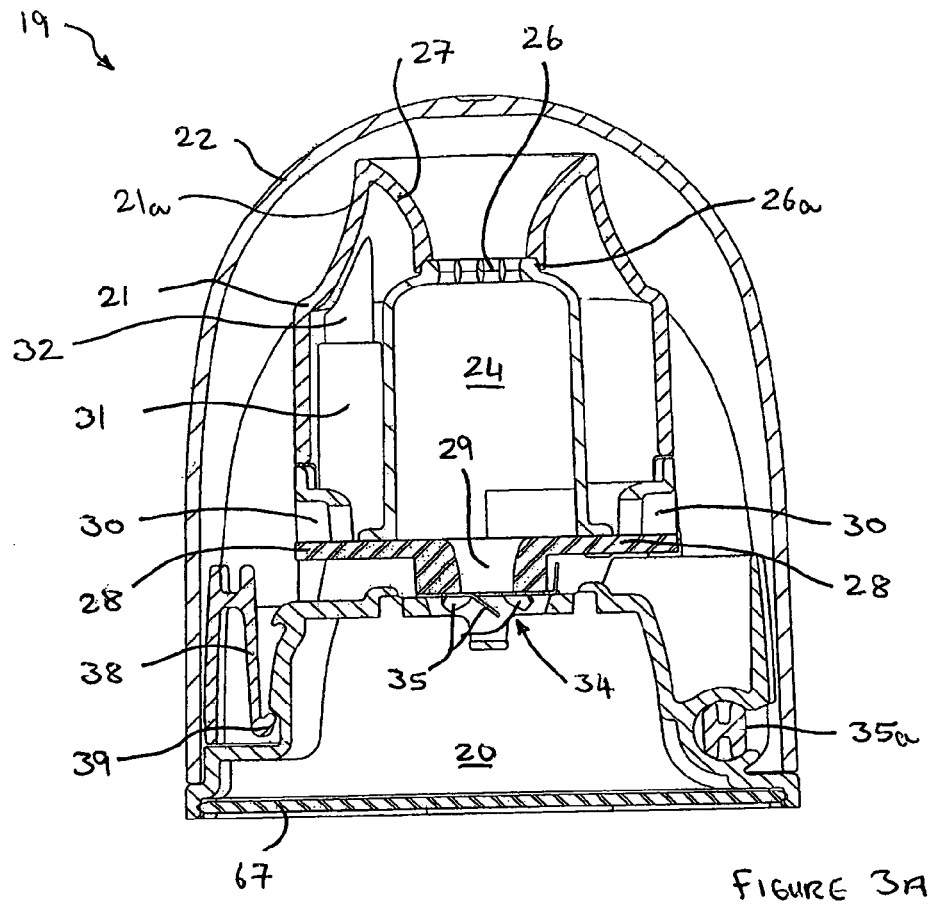
FIG. 3A is a side sectional view of the device shown in FIG. 2A.

FIG. 3A shows a vertical cross-section through the device 19 shown in FIG. 2A, and in which a cyclone chamber 24, similar to that described with reference to FIGS. 1A and 1B, is disposed within the housing 21. The cyclone chamber 24 takes the form of an insert 25, as shown more clearly in FIGS. 5A and 5B, which is received within and mounted to the housing 21. The outlet end 26 of the cyclone, which may be in the form of a mesh, has a shoulder 26a that engages with a lower edge of a curved diffuser 27 integrally formed with the mouthpiece 21a and the insert 25 is retained in position by a cyclone closure plate 28 that extends across the inlet end of the chamber 24 and has an aperture 29 therein for the flow of drug laden air into the chamber 24 from a blister during inhalation. The closure plate 28 extends over the insert 25 and closes the lower open end of the cyclone chamber 24, apart from the inlet 29, and forms the bottom wall of the bypass air flow inlets 30.

Figure 3B:
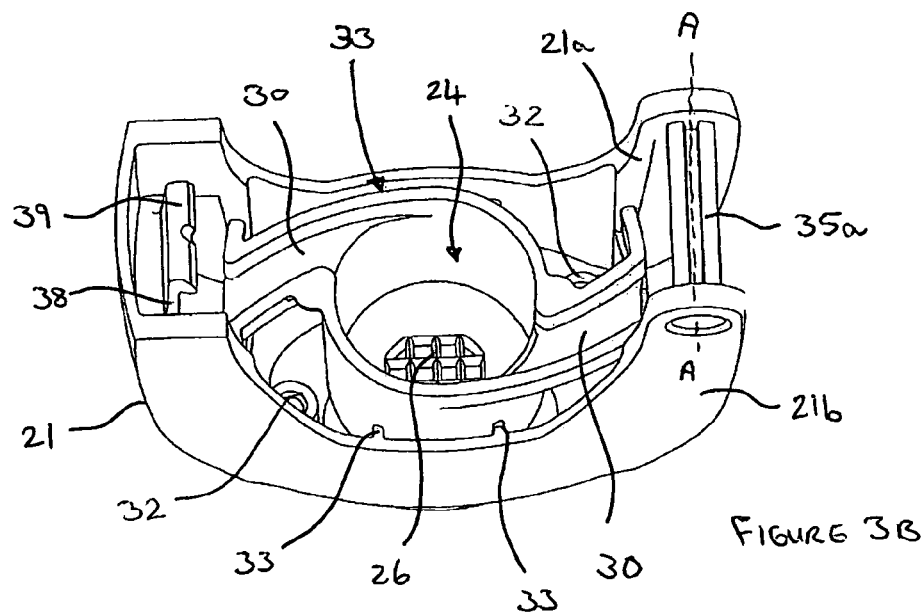
FIG. 3B is an inside perspective view of the housing with bypass air cyclone shown in FIG. 3A, with the cyclone chamber closure plate removed.

The closure plate 28 includes a pair of hollow cylindrical posts 31 upstanding therefrom alongside and outside of the chamber 24 which mate against corresponding posts 32 formed in the housing 21 (see FIGS. 3A and 3B). Screws (not shown) may be inserted into the posts 31 so that they threadingly engage with the corresponding posts 32 in the housing 21, thereby securely attaching the closure plate 28 to the housing 21 and sandwiching the cyclone chamber insert 25 therebetween. However, it will be appreciated that the insert 25 may be mounted within the housing 21 using any appropriate fastening method. Similarly, the closure plate 28 may be coupled to the insert 25 or housing 21 using any known methods of attachment. Ridges 33 (see FIGS. 3B and 4A) are formed on opposite sides of the internal surface of the housing 21 to help steady the cyclone chamber insert 25 and position it centrally within the housing 21. The ridges 33 also act as keying features to ensure correct orientational assembly of the closure plate 28 and piercing element 34 (see below) relative to the housing 21.

A blister piercing element 34 (see FIG. 3A) having downwardly directed blades 35 is mounted on the closure plate 28 below the aperture 29, i.e. on the opposite side of the closure plate 28 to the chamber 24. As is apparent from FIG. 3A, when the housing 21 is in its home position, the blades 35 extend downwardly into a space which would be occupied by the lid of a blister (not shown) received in the blister support member 20 so that, when a blister is inserted through the slot 23 and the housing 21 is returned to its home position from its primed position shown in FIG. 2B, the blades 35 puncture the lid so that the dose will be entrained in the airflow during subsequent inhalation through the mouthpiece 21a.

Figure 4A:
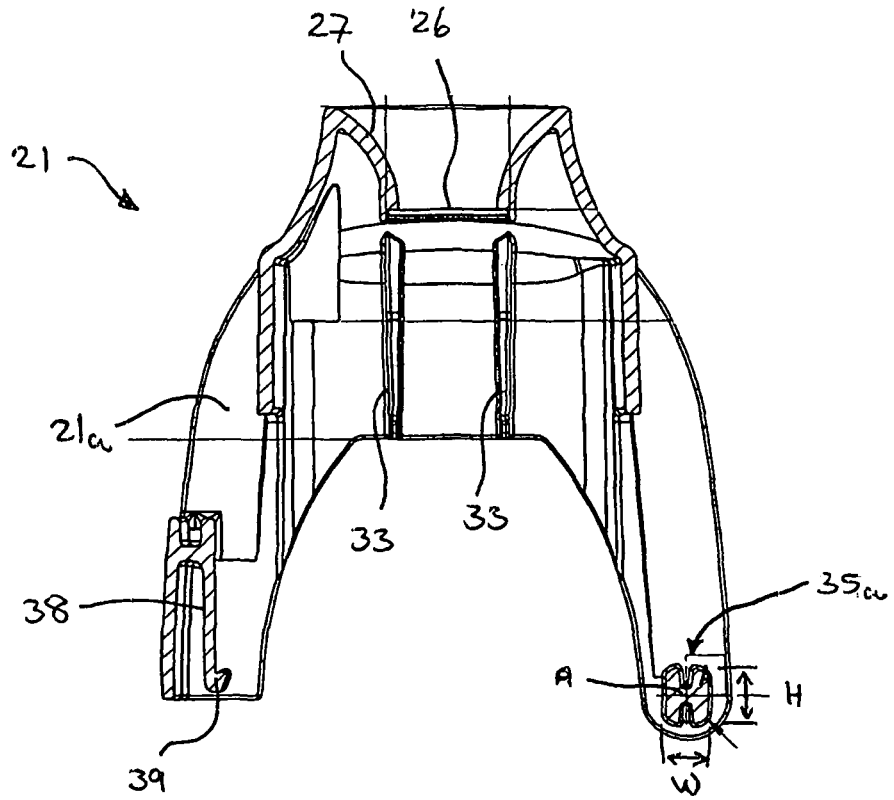
FIG. 4A is a side view of the housing used in the embodiment of FIGS. 2 and 3.
Figure 4B:
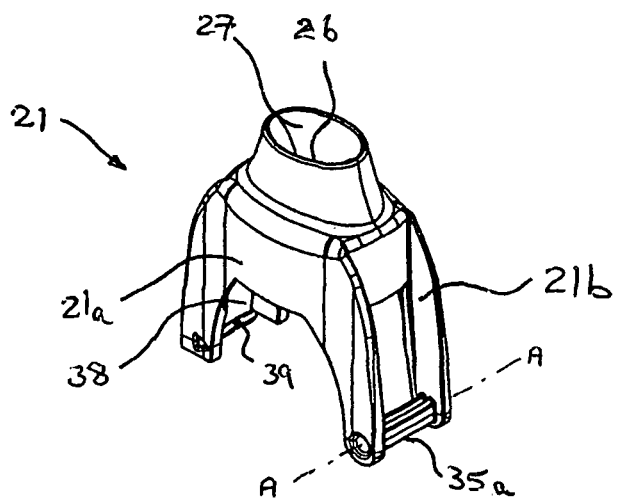
FIG. 4B is a perspective view of the housing shown in FIG. 4A.

As shown most clearly in FIGS. 4A and 4B, the housing 21 (FIG. 3B) generally has an inverted U-shape with the mouthpiece 21a at the curved end of the 'U' and with the legs of the 'U' surrounding a central portion of the blister support member 20. The cyclone chamber insert 25 is positioned within the housing 21 between facing sidewalls 21a, 21b. The bypass air inlets 30 of the cyclone chamber 24 are configured so that they open into end regions of the housing 21 between the sidewalls 21a, 21b. As the side walls 21a, 21b extend laterally beyond the end of the bypass air inlets 30, the bypass air inlets 30 will not be blocked by a person's fingers holding the device, as their fingers are spaced away from the bypass air inlet openings by the protruding side walls 21a, 21b.

Figure 5A:
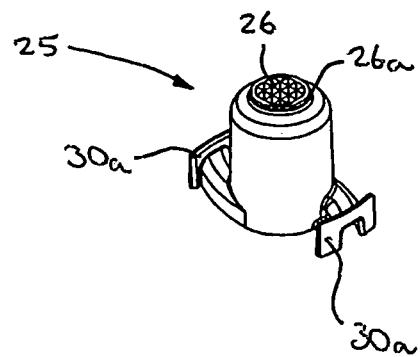
FIG. 5A is a perspective view of the bypass air cyclone chamber insert which is received in the housing shown in FIG. 4.
Figure 5B:
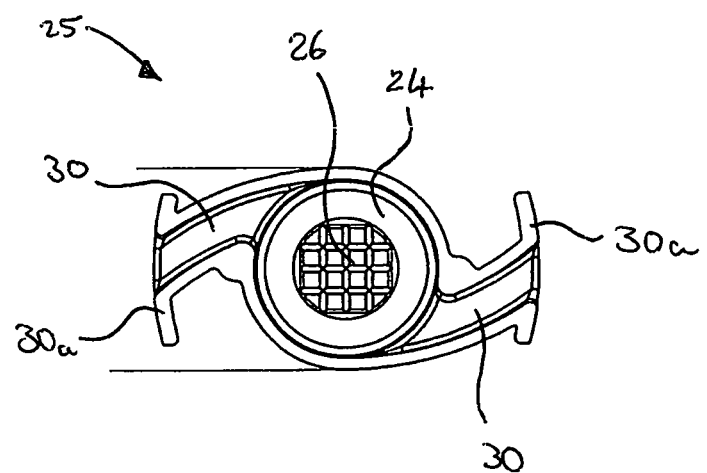
FIG. 5B is a bottom plan view of the bypass air cyclone chamber insert shown in FIG. 5A.

As can most clearly be seen from FIGS. 5A and 5B, the insert 25 is provided with arcuate shaped flanges 30a at the end of the bypass air inlets 30 that extend between the side walls 21a, 21b.

Figure 6A:
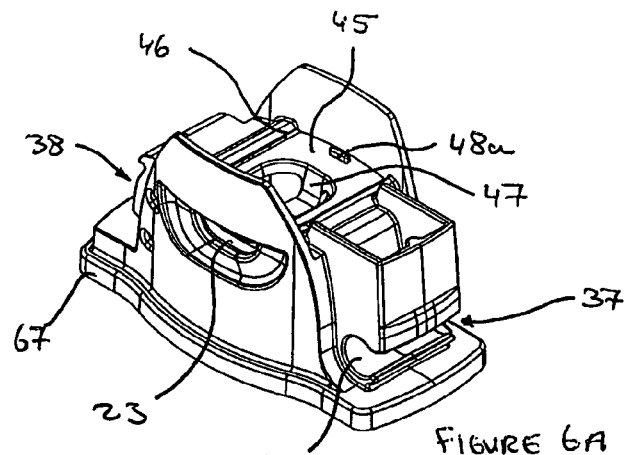
FIG. 6A is a perspective view of the blister support member of the inhalation device shown in FIGS. 2 and 3A.
Figure 6B:
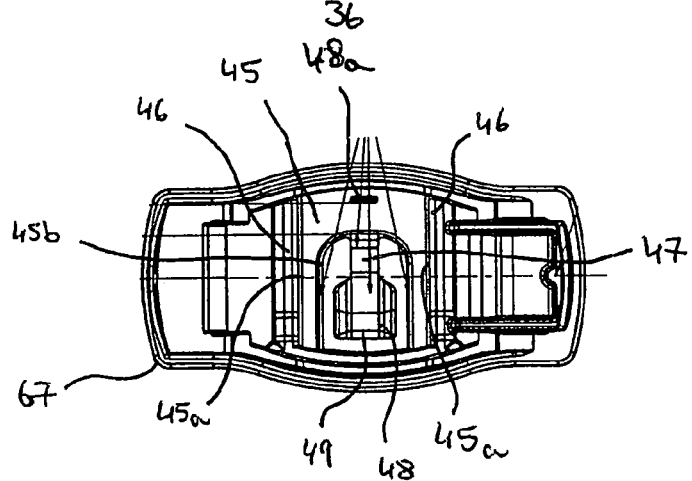
FIG. 6B is a top plan view of the blister support member shown in FIG. 6A.
Figure 6C:
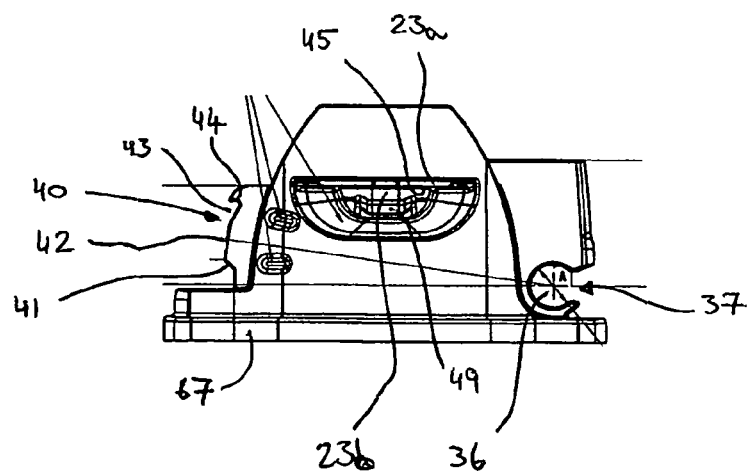
FIG. 6C is a side view of the blister support member shown in FIGS. 6A and 6B.

The housing 21 (FIG. 3B) is pivotally attached to the blister support member 20 at one lower end (at a remote end of one leg of the 'U') and includes a hub 35a that extends laterally between the side walls 21a, 21b. The housing 21 pivots about the longitudinal axis "A-A" of the hub 35 between its home and primed positions. The hub 35a is generally rectangular in cross-section so that its height 'H' is greater than its width 'W', as shown in FIG. 4A. The blister support member 20 includes a part cylindrical recess 36 (see FIG. 6C) that has an opening or mouth 37 extending along its length. The height of the opening 37 is equal to or only slightly greater than the width 'W' of the hub 35a so that the hub 35a can only be inserted into, or removed from, the recess 36 through the opening when the housing 21 is rotated into a position relative to the blister support member 20 in which the width W of the hub 35a is in alignment with the height of the opening 37 so that the hub 35a will clear the mouth of the opening 37. It will be appreciated that once the hub 35a has been inserted through the opening 37 and into the recess 36 and the housing 21 rotated relative to the base 20, it is not possible for the hub 35a to be removed from the recess 36 until the housing 21 has been rotated back into the same orientation.

The opposite end of the housing 21 remote from the hub 35a (the remote end of the other leg of the 'U') includes a resilient catch 38 which may either be formed integrally with the housing 21 or as a separate component that is attached to the housing 21 during assembly. The catch 38 has a hooked end 39 that engages with a cooperating surface 40 on the base 20 to limit rotation of the housing 21 relative to the blister support member 20 to a small angle (such as that shown in FIG. 2B) sufficient only to allow the piercing blades 35 to move by a sufficient distance to allow a blister to be inserted through the slot 23 into the blister support member 20 without fouling the blades 35 of the piercing element 34.

The cooperating surface 40 may include an initial ramp surface section 41 to provide a small degree of initial resistance to pivotal movement of the housing 21 relative to the blister support member 20 and so that the catch 38 resiliently deforms slightly as it rides over the ramp surface section 41 to enable pivotal movement of the housing 21 from its initial home position, an intermediate surface section 42 in which the deformation of the catch 38 generally remains constant during further pivotal movement of the housing 21 but which offers some degree of friction so that the housing 21 will not drop back under its own weight if released when only partially pivoted out of its home position, and an end ramp surface section 43 that terminates in a stop 44 against which the hook 39 engages when the housing 21 has pivoted its fullest extent into its open position ready for insertion of a blister. The end ramp surface section 43 ensures that at least some of the deformation of the catch 38 is released prior to the hook 39 reaching the stop 44. This ensures that the housing 21 will remain in its primed position and will not drop back into its home position too easily prior to being rotated by the patient.

Figure 6D:
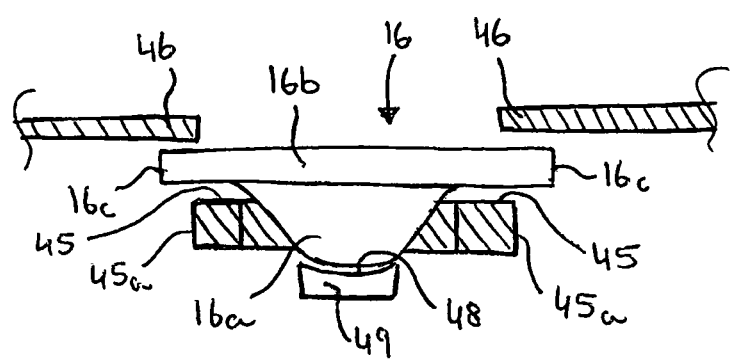
FIG. 6D shows a simplified side-sectional view through a portion of the blister support member, to illustrate how a blister is held in position between the blister support surface and the surrounding wall.

The slot 23 is in the form of a narrow slit 23a with an enlarged blister bowl-shaped central opening 23b. The blister lid and planar region surrounding the blister bowl 16a is received in the slit 23a and the blister bowl 16a passes through the central opening 23b into the device. The blister support member 20 includes a blister support surface 45 on which the planar region of the blister surrounding the blister bowl 16a sits and a surrounding wall 46. As can be most clearly seen from FIG. 6D, which shows a simplified, partial side-sectional view through a portion of the blister support member 20 with a blister held in position between the blister support surface 45 and the surrounding wall 46, the support surface 45 is positioned slightly below the surrounding wall 46 and its width, extending at right-angles to the direction of insertion of a blister into the blister support member 20, is slightly less than the width of a blister so that the edges 16c of a blister 16 overhang the side edges 45a of the blister support surface 45. The surrounding wall 46 terminates above and spaced from the side edges 45a of the support surface 45 so that the surrounding wall 46 extends over the edges of a blister thereby effectively forming a slot along either side between the blister support surface 45 and the surrounding wall 46 to receive the blister edges. The blister edges 16c are therefore held between the support surface 45 and the surrounding wall 46 to provide maximum support to the blister edges 16c surrounding the blister bowl 16a. The distance between the support surface 45 and the surrounding wall 46 of the blister support member 20 can be selected so that the blister edge is an interference fit between the support surface 45 and the surrounding wall 46 (although the distances between the support surface 45 and the blister and between the blister and the surrounding wall 46 are shown greatly exaggerated in FIG. 6D for clarity). It will also be appreciated that the surrounding wall 46 may partially overhang the support surface 45 and/or that the width of the support surface 45 may equal to or greater than the width of the blister in alternative embodiments.

The support surface 45 has a generally U-shaped open region 45b in plan view (see FIG. 6B) with a resiliently deformable cantilever arm 47 extending from the base of the 'U' towards the slot 23. In a vertical cross-section taken along the length of the cantilever arm 47, the cantilever arm 47 is generally curved in shape so as to correspond to the shape of a blister bowl 16a. The free end of the cantilever arm 47 is integrally formed with an enlarged head or tab 48 with a downwardly curved forwardly facing lip 49. The lip 49 makes initial contact with the surface of the blister bowl 16a during insertion of a blister into the slot 23b. Once initial contact has been made, further insertion causes the cantilever arm 47 to be deflected downwardly as the bowl 16a rides over the tab 48. Once the blister is fully inserted, the tab 48 has ridden back up along the opposite side of the blister bowl back towards its original position. The blister bowl 16a is thereby held or cradled snugly in position within the arcuate shape of the cantilever arm 47 ready for piercing. A stop 48a may be formed on the support surface 45 which engages with the rearmost edge of the blister to prevent over-insertion of the blister into the slot 23. As can be seen from FIG. 6D, the upper surface of the tab 48 is also arcuate in shape in a direction extending at right angles to the direction of insertion of a blister so that it conforms as closely as possible to the curved shape of the blister bowl 16a.

The blister support member 20 has a flat lower supporting surface 67 to enable the blister support member 20 to be stood upright on a table with the housing 21 upstanding from the blister support member 20. This ensures that the housing 21 need not come into contact with the surface on which the device is placed. When the housing 21 is in its home position, the longitudinal axis A-A of the chamber 24 extends substantially at right-angles to the plane of the flat lower supporting surface 67.

A second embodiment of inhalation device according to the present invention will now be described with reference to FIGS. 7A to 8C. In this embodiment, the home or storage position is also the position in which a blister is inserted into the device, i.e. the housing 60 does not need to be pivoted into a primed position to move the piercing blades out of the way to facilitate insertion of the blister. On the contrary, the housing 60 in this embodiment is only pivoted out of its home or storage position relative to the blister support member 61 after a blister has been inserted so as to pierce the blister. Once the dose has been inhaled, the housing 60 is then pivoted back into its home position to lift the piercing blades 62 out of the blister and enable the used blister to be removed from the device and a fresh one inserted ready for subsequent use. The housing 60 is relatively stable in its home position and more stable than the inhaler of the first embodiment of the invention in its primed position because the walls of the housing 60 and blister support member 61 are in alignment and the device is maintained generally upright, whereas in the first embodiment the housing is canted over at an angle away from the blister support member.

This embodiment has the advantage that the device can be pre-loaded ready for later use such as when the patient needs to take a dose in a hurry and does not have time to load the device or is incapable of loading the device at the moment a dose needs to be taken due to, for example, symptoms related to their illness. It also means that the user does not have to carry a dose separate to the inhaler.

It will be appreciated that a problem with the previous embodiment is that to maintain it in a preloaded state, the housing 21 must be kept in its primed, relatively unstable, position in which it has been pivoted away from the blister support member 20, as shown in FIG. 2B and in which the piercing blades 35 are kept out of the inserted blister. This is problematic because not only is it impossible to place the cap 22 on the device when the housing 21 is in its primed position, but it is also difficult to prevent the housing 21 from inadvertently rotating back into its home position when, for example, it is being carried in a pocket or handbag, thereby prematurely puncturing a preloaded blister.

Figure 7A:
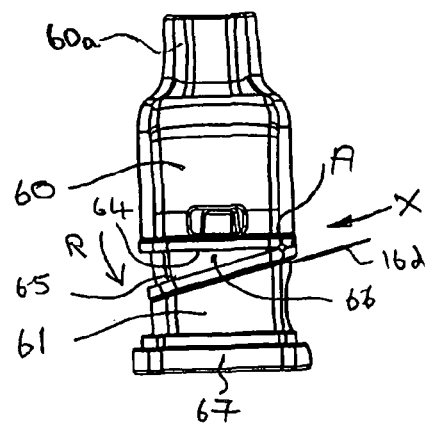
FIG. 7A is a side view of a second pre-loadable embodiment of inhalation device according to the present invention, with the housing in its home or storage position.

In the present embodiment, the slot 63 is angled relative to the longitudinal axis of the piercing member and/or cyclone chamber within the housing 60 when the housing 60 is in its home position so that rather than inserting the blister laterally through the slot 63 in the side wall of the blister support member 61 after pivoting the housing 60 out of its home position, the blister is inserted at an angle thereto relative to the longitudinal axis A-A of the chamber and of the piercing member 62, in the direction of arrow 'X' as shown in FIG. 7A, and at a downwardly directed angle in the orientation of the device as shown in the drawings. Because the blister is inserted at an angle relative to the longitudinal axis of the chamber within the housing 60, it does not foul the piercing blades 62 during insertion and the housing 60 can be maintained in an upright and aligned positon relative to the blister support member in its home position.

Figure 7B:
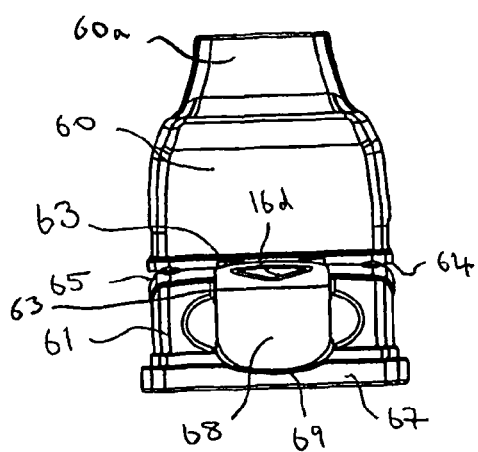
FIG. 7B is a front view of the second embodiment of inhalation device shown in FIG. 7A.
Figure 7C:
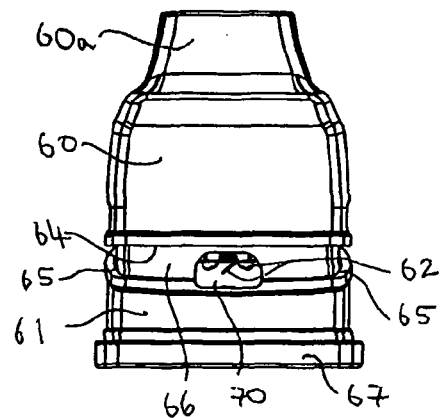
FIG. 7C is a rear view of the second embodiment of inhalation device shown in FIGS. 7A and 7B.
Figure 8A:
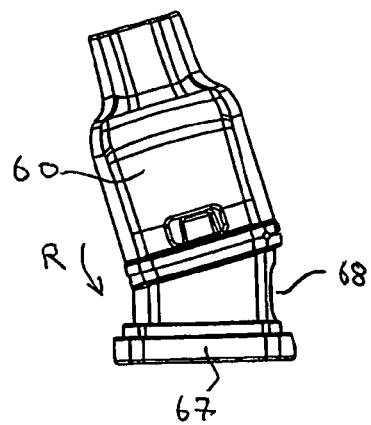
FIG. 8A is the side view of the inhalation device shown in FIG. 7A with the housing in its pierced position.
Figure 8B:
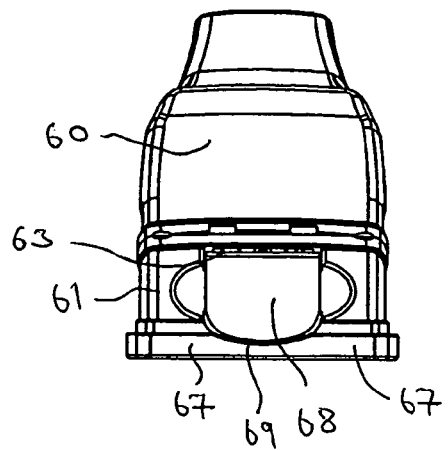
FIG. 8B is the front view of the inhalation device shown in FIG. 7B with the housing in its pierced position.
Figure 8C:
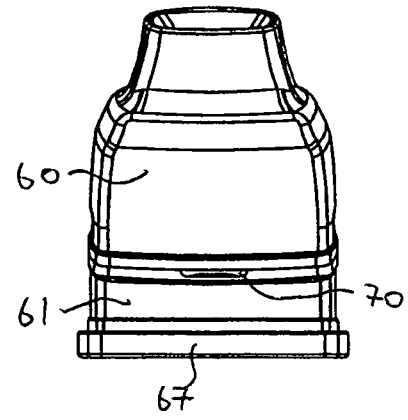
FIG. 8C is the rear view of the inhalation device shown in FIG. 7C with the housing in its pierced position.
Figure 9A:
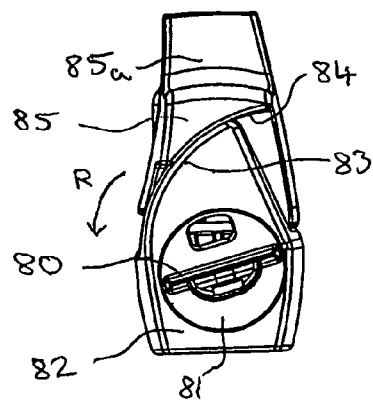
FIG. 9A is a side view of a third embodiment of inhalation device according to the present invention, with the housing in its home or storage position.
Figure 9B:
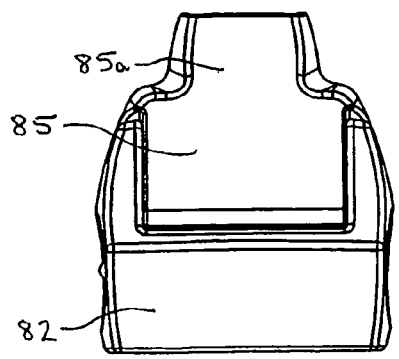
FIG. 9B is a front view of the third embodiment of inhalation device shown in FIG. 9A.
Figure 9C:
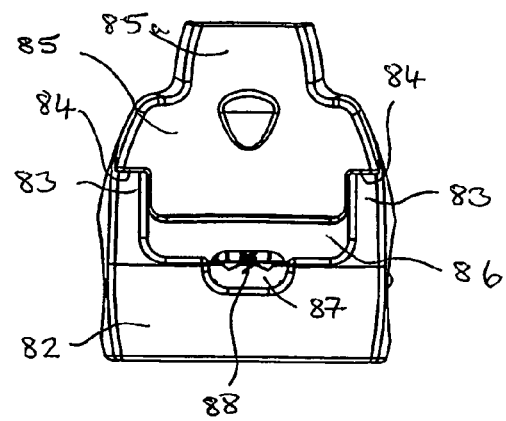
FIG. 9C is a rear view of the third embodiment of preloadable inhalation device shown in FIGS. 7A and 7B.
Figure 10A:
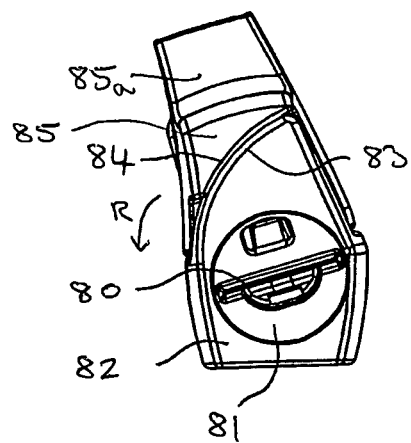
FIG. 10A is the side view of the inhalation device shown in FIG. 9A with the housing in its pierced position.
Figure 10B:
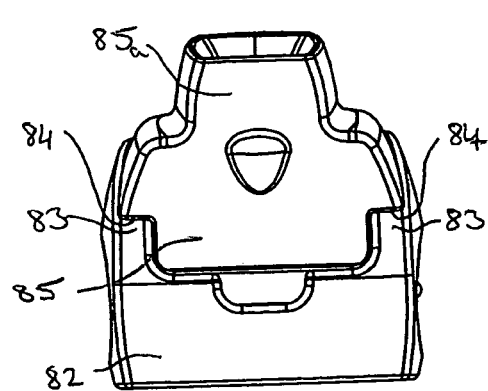
FIG. 10B is the front view of the inhalation device shown in FIG. 9B with the housing in its pierced position.
Figure 10C:
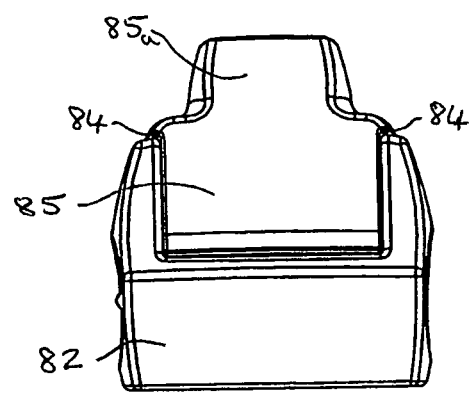
FIG. 10C is the rear view of the inhalation device shown in FIG. 9C with the housing in its pierced position.

As can be seen from FIG. 7A, the housing 60, incorporating the mouthpiece 60a, is pivotally mounted to the blister support member 61 along one long side of the device for rotation about axis 'A' and so that the housing 60 will pivot in the direction of arrow 'R' from the upright position shown in FIGS. 7A to 7C into the downwardly angled position shown in FIGS. 8A to 8C to pierce an inserted blister.

The blister support member 61 has an upper peripheral wall 65 that is angled away from the horizontal at the same angle as the slot 63 for insertion of the blister. The housing 60 also has a lower peripheral wall 64 that is horizontal when the housing 60 is in its home position and which extends at an acute angle relative to the upper peripheral wall 64 of the blister support member 61. When the housing 60 is pivoted relative to the blister support member 61, the upper peripheral wall 65 of the blister support member 61 and the lower peripheral wall 64 of the housing 60 meet and lie flush against each other. In this position the longitudinal axis A-A of the cyclone chamber is now substantially at right angles to the plane of the blister lid and the part of the blister that surrounds the blister bowl and the piercing elements are inserted through the plane of the blister lid into the blister bowl. An inner skirt 66 depends from the housing 60 within the confines of the lower peripheral wall 64 and which is received within the blister support member 61 when the housing 60 is rotated into its pierced position, as shown in FIGS. 8A to 8C.

As with the first embodiment, the blister support member 61 of the device has a lower supporting surface 67 to enable the device to be stood upright on a table or level surface.

As mentioned above, the blister may have tab 16d to facilitate its insertion into and removal from the device. If the device is preloaded ready for use, it is possible to fold part of the tab protruding from the device so that it lies flush against the side wall of the blister support member 61. As shown in FIG. 7B, the side wall of the blister support member 61 may include a recess 68 to receive the folded tab 16d and the edge of the recess may have a lip 69 behind which the tab can be pushed to retain it in position against the side wall of the blister support member 61 until the blister needs to be removed.

An opening 70 is formed in the skirt 66 between the housing 60 and the blister support member 61 so that a patient can see into the device and visibly check to determine whether a blister is located therein and also whether it has already been pierced or not, as well as see the piercing elements 62 to check for damage or dirt.

A third embodiment of inhalation device will now be described with reference to FIGS. 9A to 10C. This embodiment is similar to the second embodiment and so like features will not be described again in detail. In this embodiment, the blister is again inserted at an angle to the horizontal or to the longitudinal axis of the cyclone chamber in its home or storage position but the slot 80 is in a shorter side wall of the device rather than in a longer front or rear wall, although the housing 85, incorporating the mouthpiece 85a, is still pivotally mounted to the blister support member 82 along an axis extending along a long side of the device.

Furthermore, the slot 80 is recessed within a bowl or hemispherically shaped depression 81 formed in the blister support member 82 so that the tab 16d of a blister does not protrude beyond the side walls of the device when a blister is inserted into the device. Therefore, it is not necessary to fold the blister tab 16d to move it out of the way in this embodiment. The bowl or depression 81 is of a size and configuration to enable a patient to insert a thumb and index finger therein on either side of a blister tab 16d so as to grasp the tab 16d and withdraw the blister from the device.

In the third embodiment, the blister support member 82 of the device is provided with upwardly facing convex shaped supporting walls 83 which mate with correspondingly shaped downwardly facing concave surfaces 84 formed on the housing 85. As the housing 85 is pivoted (in the direction of arrow 'R' from its home position shown in FIGS. 9A to 9C into its pierced position shown in FIGS. 10A to 10C) after insertion of a blister, the concave surfaces 84 of the housing 85 ride over the convex shaped supporting walls 83, thereby guiding movement of the housing 85 and ensuring that it is fully supported throughout its full range of movement.

As with the previous embodiment, the housing 85 has a skirt 86 that is received within the blister support member 82 and slides within it during pivotal movement of the housing 85. The skirt 86 has an aperture 87 to enable a user to see the piercing element 88 and also to enable them to ascertain whether a blister located in the device has already been pierced or not.

A fourth embodiment will now be described with reference to FIGS. 11 to 19 of the accompanying drawings. In this embodiment, the housing and the base are fixed relative to each other and the blister is received in a blister support member that has a lever portion extending from within the housing and which is pivotally mounted with respect to the housing and the base. An advantage of this embodiment over the previous embodiments is that the housing, together with the bypass cyclone, remains stationary and only the blister support element, together with the blister mounted thereto, is rotated to pierce the blister. The housing contains and mounts a bypass cyclone and blister piercing element, as previously described with reference to the previous embodiments and FIGS. 1A and 1B.

Figure 11:
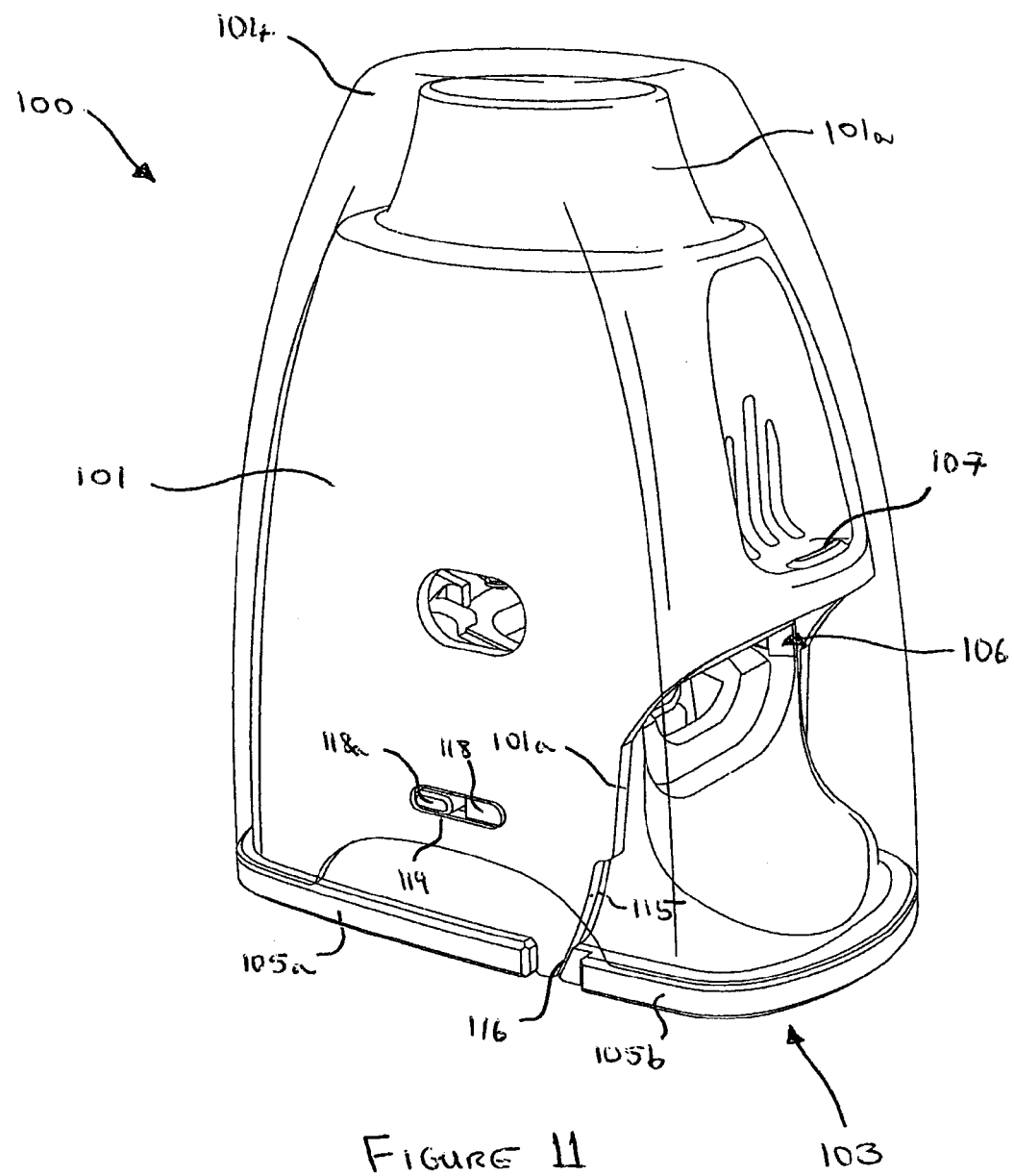
FIG. 11 is a perspective view of a fourth embodiment of a unit-dose inhalation device of the present invention with the housing in its first storage or home position and with a cap in place over the housing and the blister support member.

Referring to the drawings, FIG. 11 shows a perspective view of an inhalation device 100 according to the fourth embodiment having a housing 101 including a mouthpiece 101a, a base part 102 (see FIG. 14) immovably attached to the housing 101 and a pivotally mounted blister support member 103 which is received within the housing 101 and held in place by the base 102. The blister support member 103 has a lever portion 103a that protrudes from a cut-out 101a formed in the wall of the housing 101. A cap 104 (shown as being transparent in FIG. 11) extends over the housing 101 and locates on a shoulder 105 having a first part 105a formed at the lowermost edge of the housing 101 and a second part 105b formed at the lowermost edge of the portion 103a of the lever portion 103a that protrudes from the housing 101. The cap 104 thereby substantially covers the whole of the device, apart from the shoulder 105.

Figure 12:
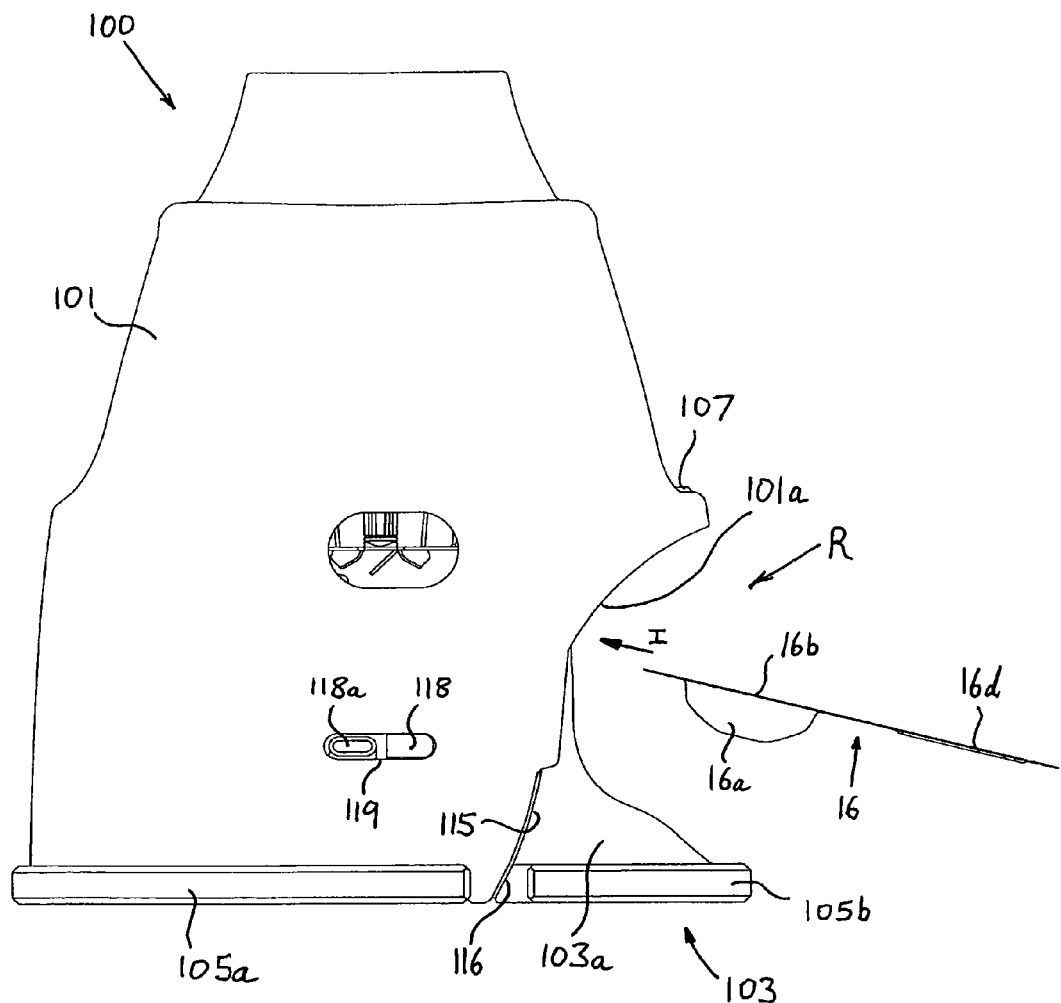
FIG. 12 is a side view of the inhalation device shown in FIG. 11 with the cap removed and showing a blister about to be inserted into the device.
Figure 13:
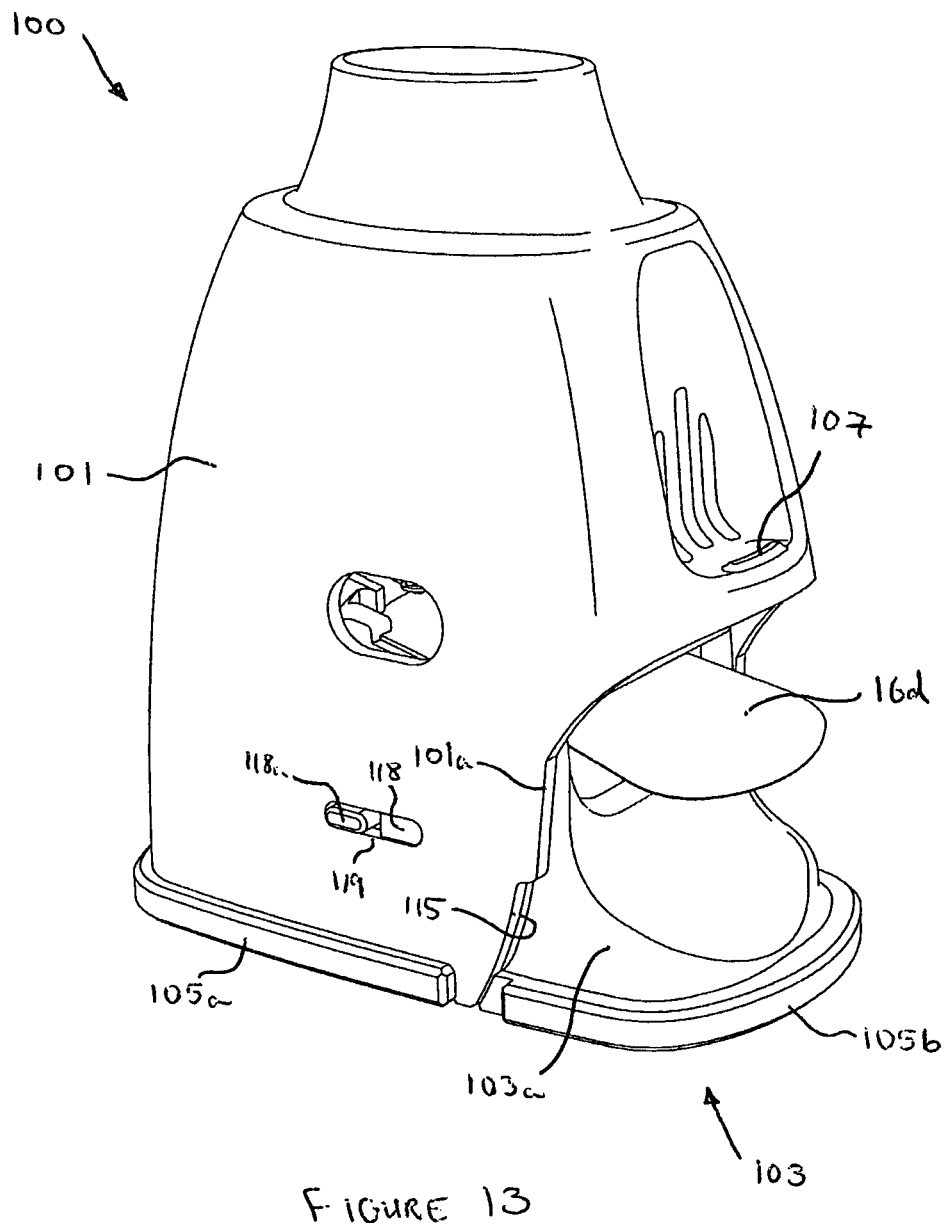
FIG. 13 is a perspective view of the inhalation device shown in FIGS. 11 and 12 with a blister inserted therein.

FIGS. 11 and 12 show the device with the lever portion 103a in its home or storage position in which the device is ready to receive a blister 16 by inserting it into the device through a slot 106 formed in the blister support member 103, in the angled direction of arrow 'I' shown in FIG. 12. FIG. 13 shows the device once a blister 16 has been fully inserted therein but prior to piercing. It will be noted that the blister support member 103 and the housing 101 together define a roughly hemispherically shaped recess 'R' in the side of the device and the tab 16d of the blister extends into this recess when the blister 16 is fully inserted into the device 100. This enables the cap 104 to be located over the device 100 so as to locate against shoulder 105 even when a blister 16 is received within it, with the blister tab extending into said recess without interference from the cap 104. As can be seen from the cross-sectional view of FIG. 14, the blister tab 16d does not extend beyond the outer surface of the housing 101 or lever portion 103a and so does not come into contact with the cap 104. Therefore, the device 100 can be made-ready for later use (i.e. pre-loaded) by removing the cap 104, inserting a blister 16 into the device and by replacing the cap 104. It will be noted that the device remains in a stable position even when a blister has been inserted therein and it does not need to be primed i.e. moved into an unstable position to allow a blister to be inserted.

Figure 14:
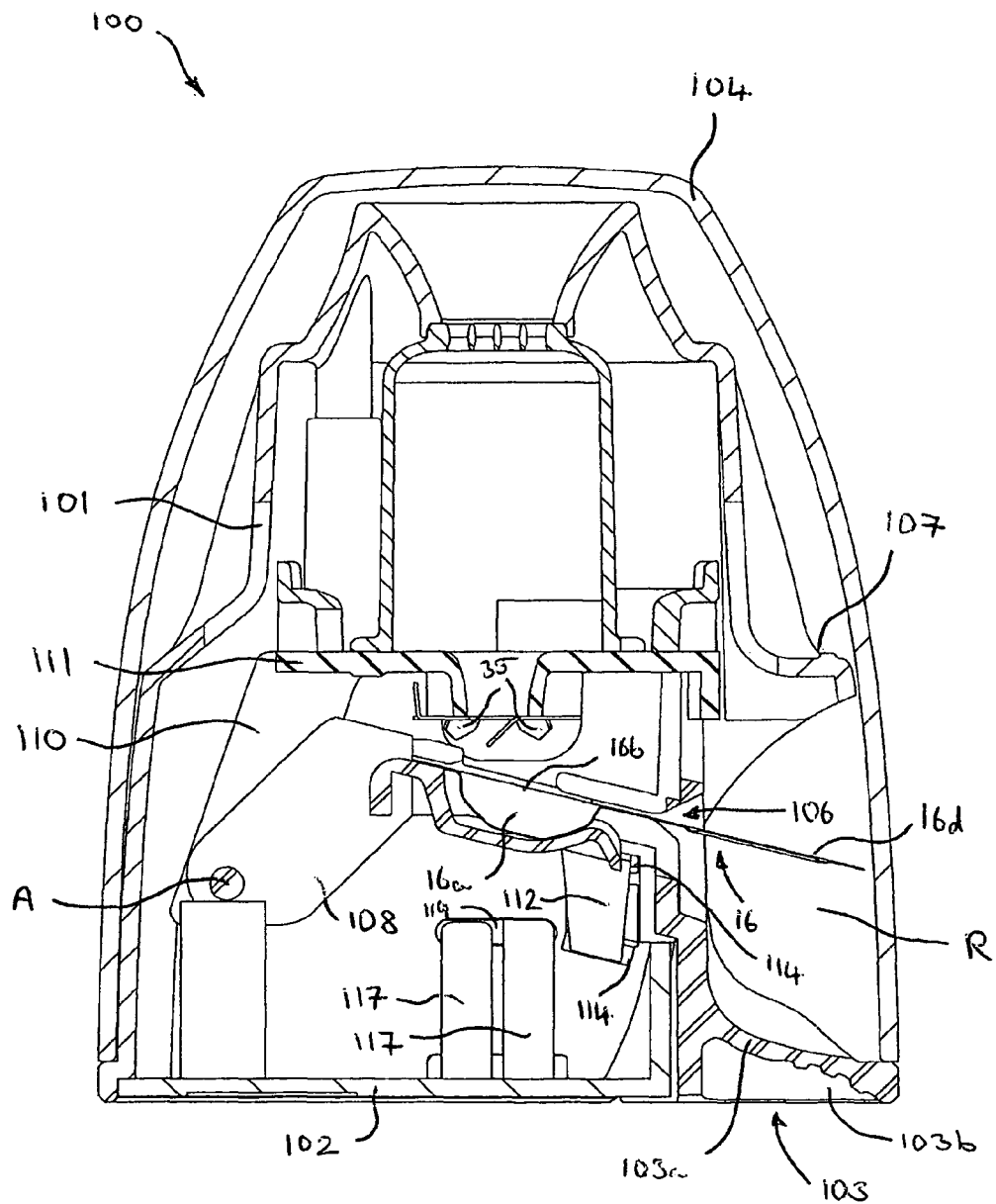
FIG. 14 is a cross-sectional view of the inhalation device of FIGS. 11 to 13 with a blister inserted therein.
Figure 15:
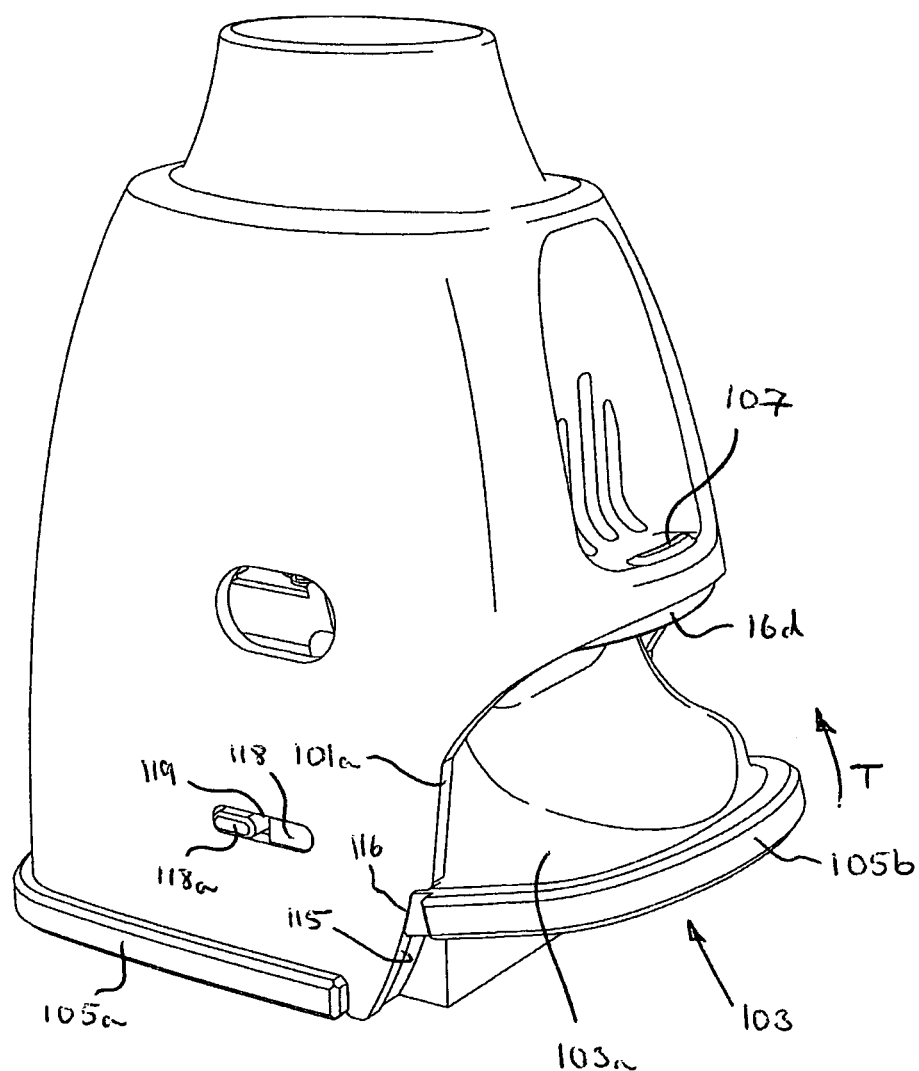
FIG. 15 is a perspective view of the inhalation device of FIGS. 11 to 14 with the blister support member rotated into its pierced position.
Figure 16:
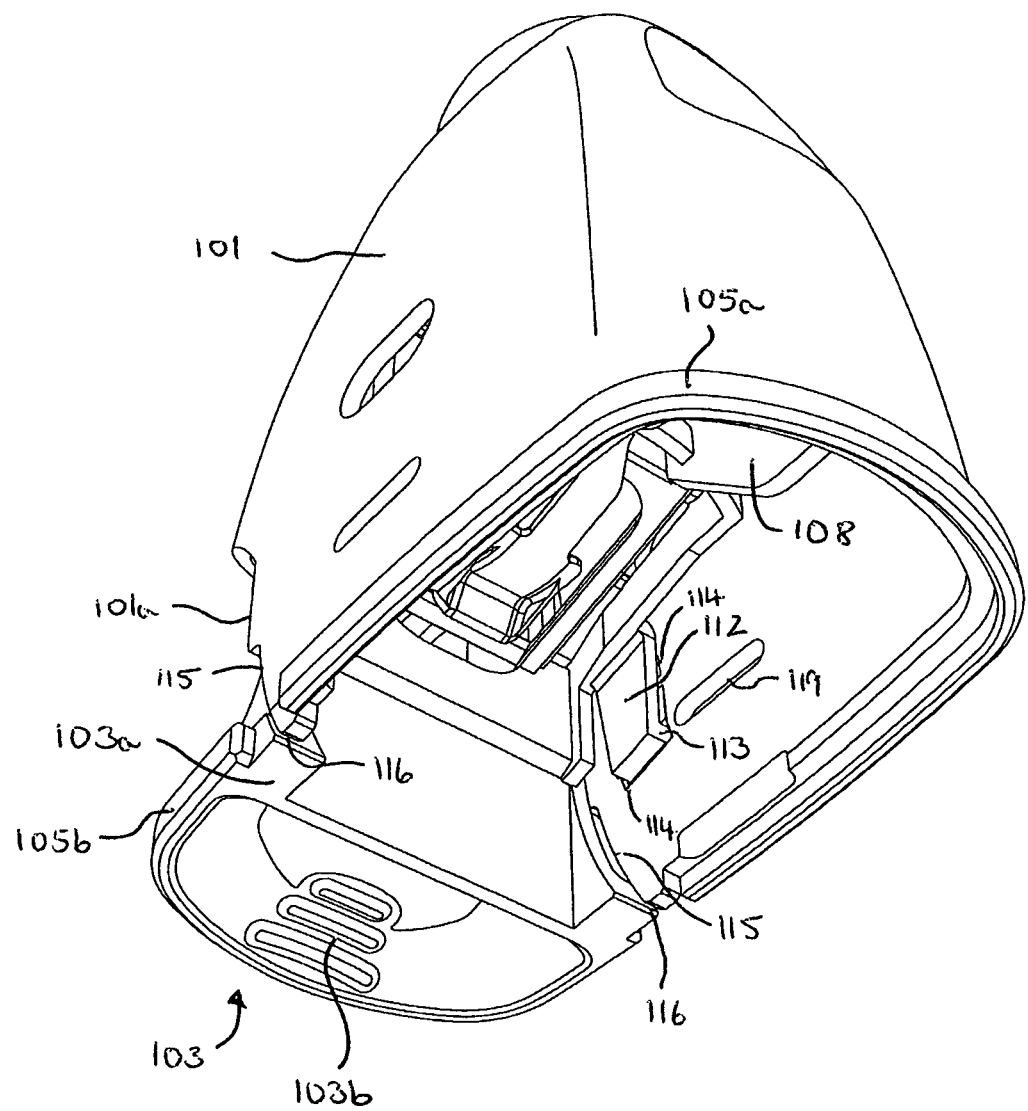
FIG. 16 is a bottom perspective view of the inhalation device of FIGS. 11 to 16, with the blister support member and base removed.

FIG. 14 shows a cross-sectional view through the device with a blister 16 inserted therein and from which it can be seen that the blister bowl 16a is positioned below the blister piercing elements 35. To pierce the blister 16, the blister support member 103 is rotated by rotating the lever portion 103a in the direction of arrow 'T' and into the position shown in FIG. 15. This can be achieved by placing a thumb on the underside 103b of the lever element 103 and a finger on a reaction surface 107 formed on the housing 101 on the opposite side of the recess R. By squeezing the thumb and finger together, the blister support member 103 rotates into the position shown in FIG. 15 together with the blister 16. When the position shown in FIG. 15 is reached, the blister tab 16d is located towards the top of the cut-out in the mouthpiece 101 and directly beneath the reaction surface 107. As the tab 16d is made relatively inaccessible in this position, a user is less inclined to attempt to pull on it so as to try and remove the blister 16 from the device whilst the blister support member 103 is in its pierced position.

The blister support member 103 has a support structure for the blister and blister bowl which is similar to that described with reference to the previous embodiments (with reference to FIGS. 6A to 6D) and so a description of it will not be repeated again here. However, in this embodiment, the blister support member 103 has a pair of spaced parallel legs 108 extending from the blister seat and an axle 109 extending between the legs 108 having protruding portions 109a extending from opposite sides thereof. The protruding portions 109a locate in openings formed in a corresponding pair of legs 110 depending from the cyclone element closure plate 111 (see FIG. 14) so as to define an axis 'A' about which the blister support member 103 can rotate between its first, stable or home position and its, second, pierced position.

The blister support member 103 is also provided with a pair of resilient arms 112 depending from each side. Each arm 112 has a tongue 113 at its free end. A pair of spaced detents 114 are also formed on opposite sides on the inner wall of the housing 101 (see FIG. 18) and positioned so that, when the blister support member 103 is in its home position, the tongue 113 of each arm 112 is received in one detent 114 and, when the blister support member 103 is in its pierced position, the tongue 113 is received in the other detent 114, the arm 112 resiliently deforming when the blister support member 103 is pivoted so that the tongue 113 is lifted out of one detent 114 and drops into the other detent 114 when the pierced position has been reached. The cooperation between the tongue 113 and the detents maintains the blister support member 103 in either its home or pierced position and ensures that the blister support member 103 will only rotate when sufficient force is applied to it in order to overcome the resilience of the arms 112 and lift the tongues 113 out of their detents 114. As the tongues 113 slide against the inner wall of the housing 101 between detents 114, this creates friction which prevents the blister support member 103 from falling under its own weight back into its home position, if it were to be released prior to reaching the pierced position.

Figure 17:
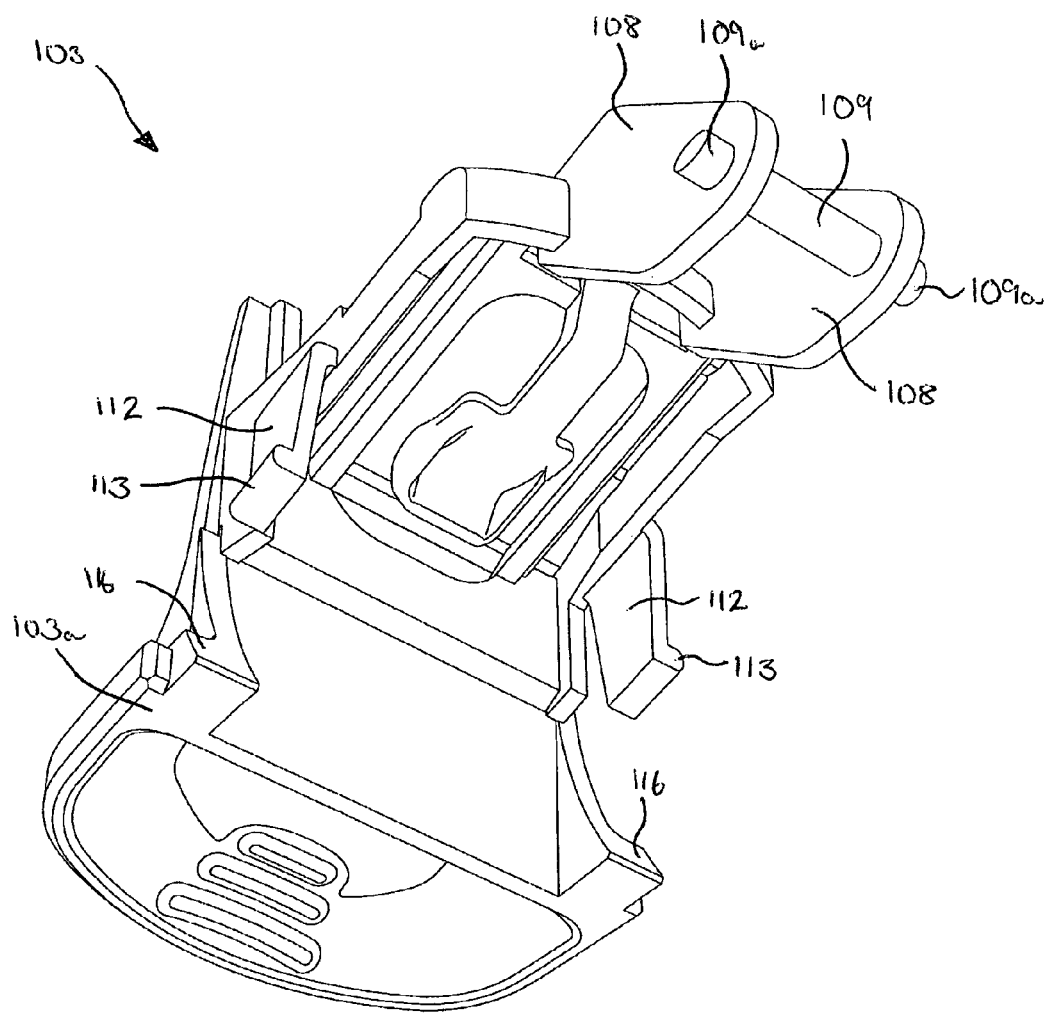
FIG. 17 is a bottom perspective view of the blister support member forming part of the inhalation device of FIGS. 11 to 16.
Figure 18:
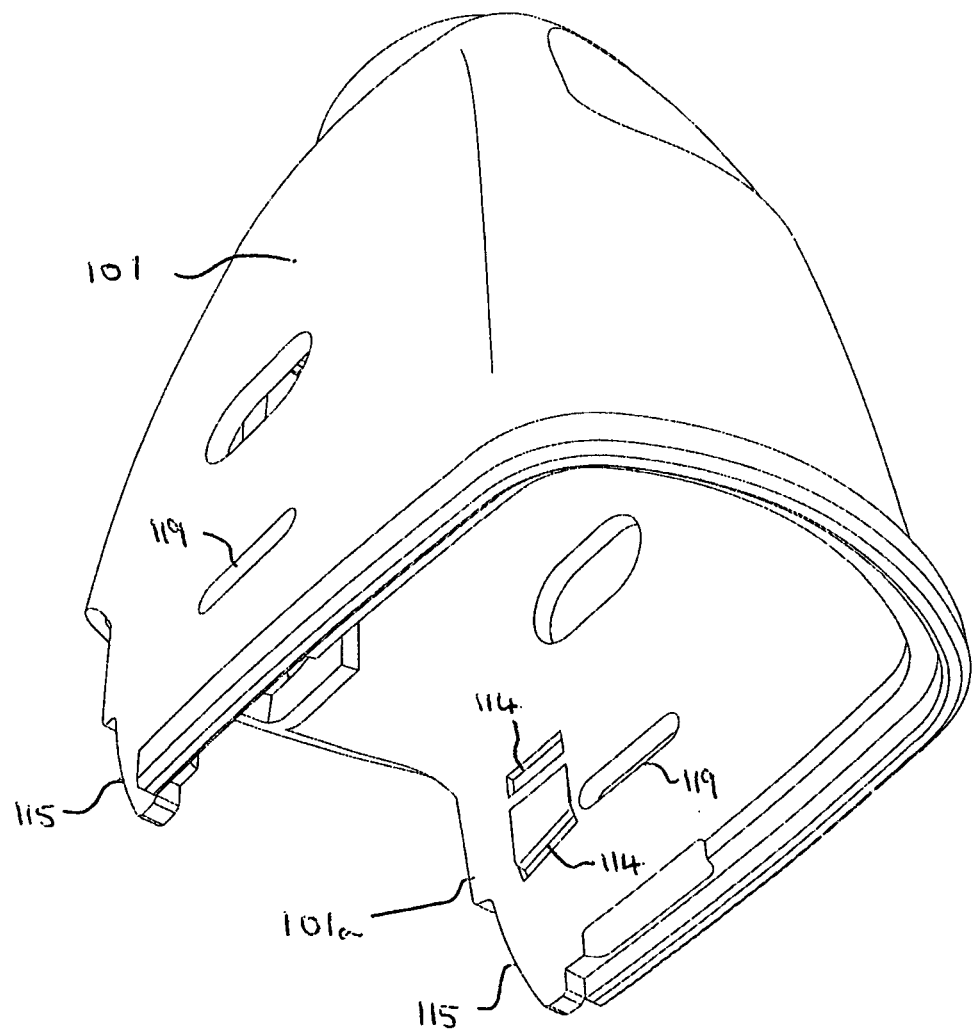
FIG. 18 is a bottom perspective view of the housing forming part of the inhalation device of FIGS. 11 to 17.

As can be seen most clearly from FIGS. 13 and 17, the housing 101 has an arcuate guide surface 115 and the blister support member 103 has a corresponding guide member 116 that slideably cooperates with the guide surface 115 so as to guide pivotal movement of the blister support member 103 relative to the housing 101.

Figure 19:
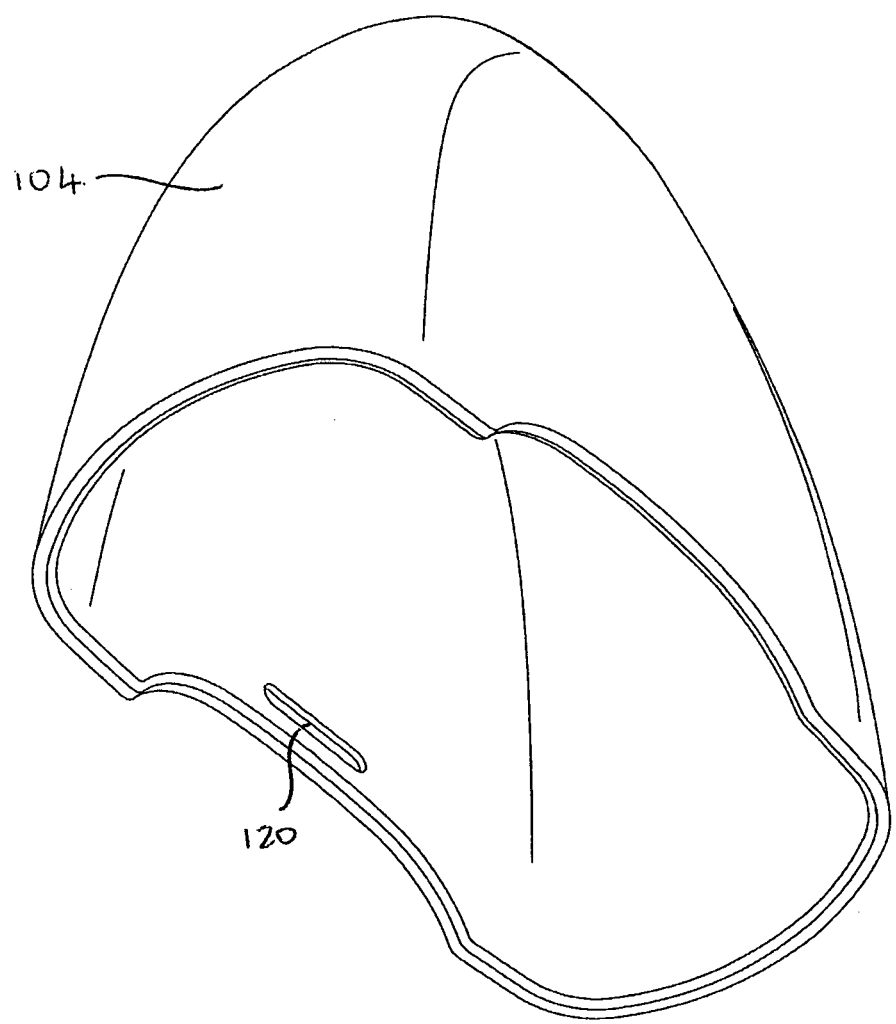
FIG. 19 is a bottom perspective view of the cap shown in FIG. 11.

The base 102 may removably clip onto the housing 101. In particular, the base 102 is provided with a pair of resilient uprights 117 on each side, each upright having a head portion 118 that locates in an elongate aperture 119 in the housing 101. One of the head portions 118a protrudes through the aperture 119 so as to be slightly raised above the outer surface of the housing 101 and functions so as to hold the cap 104 in position over the device. This means that the cap 104 need not be a friction fit with the outer surface of the housing 101. It also ensures that, when a user removes the cap 104 from the device, pressure is applied only to the head 118a of the resilient upright 117 protruding through the housing 101 so as to deform that upright 117 and not the housing 101 itself. As shown in FIG. 19, the cap 104 also has a detent 120 formed in its inner surface to receive the head portion 118a when the cap 104 is positioned on the device 100.

It will be appreciated that the cap 104 cannot be located over the device 100 when the blister support member 103 is in its pierced position. If an attempt is made to locate the cap 104 over the device 100 whilst the blister support member 103 is in its pierced position, the cap 104 will push against the blister support member 103 and cause it to rotate back into its home position as the cap 104 slides onto the device 100.

Figure 20A:
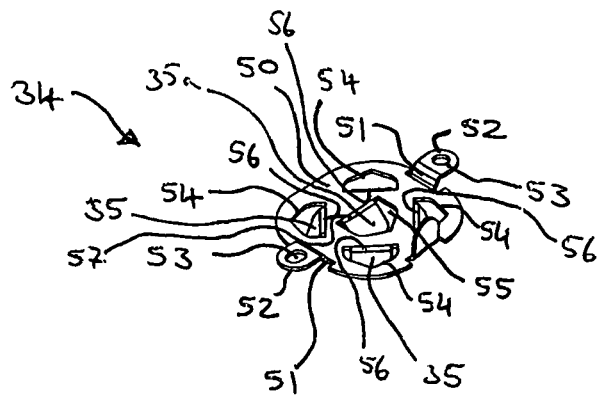
FIG. 20A is a perspective view of a blister piercing member for use with any embodiment of the inhalation device of the invention.
Figure 20B:
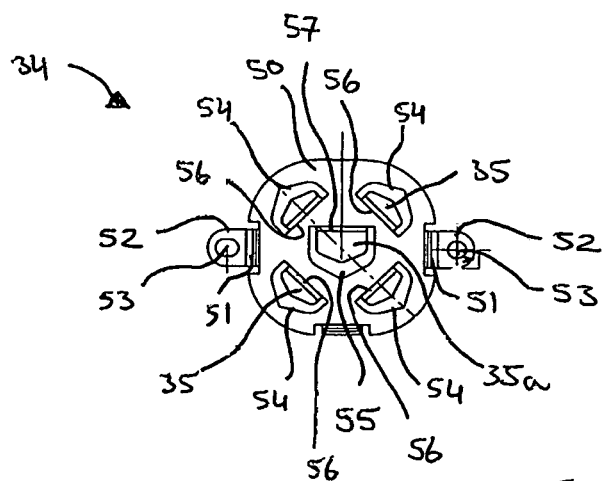
FIG. 20B is a top plan view of the blister piercing member shown in FIG. 20A.
Figure 20C:
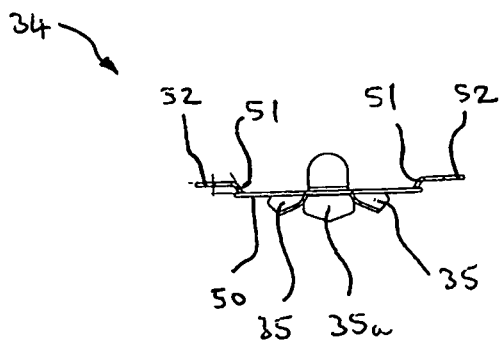
FIG. 20C is a side view of the blister piercing member shown in FIGS. 20A and 20B.

A preferred blister piercing member 34 for use with any inhalation device, including those of the present invention, is shown in FIGS. 20A to 20C and will now be described in more detail. The piercing member 34 is stamped from a flat plate 50 to form piercing blades 35 that depend downwardly out of the plane of the plate 50. Mounting arms 51 also extend laterally from the edges of the plate 50 at an angle to the plane of the plate 50. Tabs 52 extend from the free ends of the arms 51 in a plane parallel to the plane of the plate 50 and holes 53 are formed in the tabs 52 to facilitate connection of the piercing member 34 to the closure plate 28 during assembly so that the plate 50 is spaced from the surface of the cyclone chamber insert closure plate 28. As is apparent from FIGS. 20A and 20B, the piercing member 34 has four clean air inlet flow openings 54 spaced equidistantly and symmetrically around a central drug laden air outlet opening 55 so that clean air enters the blister bowl 16a through the air inlet flow openings 54 and entrains the dose contained in the blister bowl 16. The drug laden air then flows out of the blister bowl 16a through the central drug laden air outlet opening 55. The drug laden air outlet opening 55 is connected to the drug laden air inlet port 29 of the chamber 24 so that the drug laden air flows in an axial direction into the chamber 24. The peripheral clean air inlet flow openings 54 are isolated from the central drug laden air outlet opening 55 when the piercing member 34 has been mounted to the closure plate 28 so that all the drug laden air flows through the drug laden air outlet opening 55 and via the drug laden air inlet port 29 into the chamber 24.

It will be appreciated from FIGS. 20A and 20B, that the blades 35 of the peripheral drug flow inlet openings 54 are all the same size and shape and are formed by bending them out of the plane of the plate along edges or fold lines 56 that connect the blades to the plate 50. Each blade 35 is folded out of the plane of the plate 50 by the same angle of approximately 45 degrees. The fold lines 56 of opposite, non-adjacent blades 35 are parallel to each other whereas the fold lines of adjacent blades 35 are arranged at an angle of 90 degrees to each other so that they are oriented symmetrically. The blade 35a forming the central drug laden air outlet opening 55 also depends from the plane of the plate 50 along a fold line 57. Fold line 57 preferably extends at 45 degrees to each of the fold lines 56 of the drug flow inlet openings 54. The drug flow outlet opening 55 and its corresponding blade 35a may be larger than each of the drug flow inlet openings 54 and their corresponding blades 35.

Although the device according to the embodiments of FIGS. 7A to 19 are intended to be preloadable, as explained above, it is also envisaged that it could be used in the same way as the first embodiment of FIGS. 2A to 6D and in which a blister is inserted into the device immediately prior to use.

Although not shown in the embodiments of FIGS. 7A to 10C, it will be appreciated that the device may be provided with a cap, as with the first embodiment. The cap may be placed over the mouthpiece and base of the device irrespective of whether a blister has been inserted into the device ready for piercing at a later time.

It will be appreciated that the foregoing description is given by way of example only and that modifications may be made to the support assembly of the present invention without departing from the scope of the appended claims.

The invention claimed is:

1. An inhaler comprising a housing having a mouthpiece through which a user may inhale a dose of medicament and a blister support member having a slot to receive a dose containing blister, the housing and the blister support member being pivotable relative to each other between a first position for insertion of a blister into said slot and, a second, pierced position, in which a blister piercing element carried by the housing pierces an inserted blister so that when a user inhales on the mouthpiece, the dose is entrained in an airflow and flows out of the blister through the mouthpiece and into the user's airway, wherein the housing comprises a substantially cylindrical chamber having an inlet at one end for the flow of drug laden air into the chamber from a pierced blister and an outlet at its opposite end for the flow of drug laden air out of the mouthpiece and into a patient's airway.

2. An inhaler according to claim 1, wherein the blister support member is pivotally mounted within, and extends from, the housing to enable a user to pivot the blister support member relative to the housing into said second, pierced position so that a blister inserted into the slot and supported by the blister support member is pierced by said blister piercing element.

3. An inhaler according to claim 2, wherein the blister support member includes a lever portion that extends into a cut-out section formed in a wall of the housing.

4. An inhaler according to claim 3, wherein the lever portion fills only a portion of the cut-out section in the wall of the housing such that the housing and the lever portion together define a recess therebetween.

5. An inhaler according to claim 4, wherein the slot is located such that a blister tab of a blister received in the blister support member protrudes from said slot into said recess.

6. An inhaler according to claim 5, wherein the slot is configured such that a blister tab extending into said recess is spaced from the housing and from the blister support member when the blister support member is in its first position.

7. An inhaler according to claim 6, wherein the blister support member and the housing is configured such that, when the blister support member is rotated into its second, pierced position, a blister tab protruding from the aperture into the recess is in a less accessible position than when the blister support member is in its first position.

8. An inhaler according to claim 3, wherein the housing has opposite end walls and the cut-away section is formed in one of said end walls, the lever portion extending into said cut-away section.

9. An inhaler according to claim 8, wherein the housing has a lower end remote from the mouthpiece, said lower end comprising a laterally protruding shoulder to support a protective cap located over the housing.

10. An inhaler according to claim 9, wherein the lever portion also includes a shoulder that forms an extension of the shoulder on the housing when the lever portion is in its first position, such that a cap is supported by both the shoulder on the housing and the shoulder extension on the lever portion.

11. An inhaler according to claim 10, wherein the protective cap extends over the recess formed by said cut-away section of the housing and said lever portion without interfering with a blister tab of a blister received in the housing and extending into said recess.

12. An inhaler according to claim 10, wherein the cap contacts the shoulder on the lever portion when the cap is placed over the housing and, if the lever portion is in its second position, rotates the lever portion back into its first position.

13. An inhaler according to claim 3, wherein arcuate guide surfaces are formed on the housing, the lever portion having a cooperating guide member that slides along the guide surfaces to guide movement of the lever portion between its first and second positions.

14. An inhaler according to claim 3, wherein the blister support member includes a resilient arm having a tongue at its free end that is biased against the inner surface of the housing, the housing having detents positioned such that said tongue locates in respective detents when said blister support member is in its first and second positions.

15. An inhaler according to claim 3, comprising a base member that closes a lower end of the housing remote from the mouthpiece, said base member having a wall to support the housing upright on a flat surface.

16. An inhaler according to claim 15, wherein the lever portion has an underside that forms a continuation of said wall of the base member when said lever portion is in its non-pierced position such that, when the inhaler is placed upright on a flat surface, the inhaler is supported by said wall and the underside of the lever portion.

17. An inhaler according to claim 15, wherein the blister support member contacts the base member in its first position and prevents the blister support member from rotating beyond said first position in a direction away from its second position.

18. An inhaler according to claim 15, wherein the base member comprises a resilient arm that extends upwardly within the housing from the wall of the base member, the free end of said arm having a tongue that engages in an opening in the housing to attach the base to the housing.

19. An inhaler according to claim 18, wherein the tongue protrudes through the opening beyond the outer surface of the housing to contact a cap located over the housing.

20. An inhaler according to claim 1, wherein the housing is pivotable by a user relative to the blister support member between said first and second positions.

21. An inhaler according to claim 20, wherein the blister support member comprises a seat to support a blister that has been inserted through the slot in its first position.

22. An inhaler according to claim 1, wherein the chamber has a longitudinal axis that extends between the inlet and the outlet.

23. An inhaler according to claim 22, wherein the substantially cylindrical chamber has at least one bypass air inlet for the flow of clean air into the cyclone chamber to interact with the drug laden air flowing between the inlet and the outlet.

24. An inhaler according to claim 23, wherein the bypass air inlet(s) meet the chamber at a tangent so that a cyclonic air flow is generated from clean air around the drug laden air flow.

25. An inhaler according to claim 22, wherein the chamber and bypass air inlets comprise an insert located within the housing.

26. An inhaler according to claim 25, wherein the housing comprises a pair of spaced side walls with the insert being located between the side walls, the side walls extending laterally beyond the ends of the bypass air inlets.

27. An inhaler according to claim 21, when dependent on claim 20, wherein the housing has a stable home or storage position in which the housing is located in a lowered position against the blister support member and the blister piercing element is in a position in which a blister located in the blister support member is pierced by the piercing elements.

28. An inhaler according to claim 27, wherein the housing has an unstable primed position in which it is pivoted relative to the blister support member out of its home or storage position into a raised position in which the housing is angled relative to the blister support member and in which the blister piercing element is moved out of a blister pierced position to enable a blister to be inserted into the blister support member through said slot and subsequently removed therefrom.

29. An inhaler according to claim 27, wherein the longitudinal axis of the chamber is substantially at right-angles to the direction of insertion of a blister into the blister support member, when the blister support member is in its stable home or storage position.

30. An inhaler according to claim 27, wherein a cap is positionable over the housing and the blister support member only when the housing is in its stable home or storage position.

31. An inhaler according to claim 1, when dependent on claim 20, wherein the housing has a home or storage position in which the housing is raised relative to the blister support member and the direction of insertion of a blister into the slot is angled relative to the longitudinal axis of the chamber.

32. An inhaler according to claim 31, wherein the housing has a pierced position in which it is pivoted out of its home or storage position into a lowered angled position against the blister support member in which the blister piercing elements assume a blister pierced position to pierce a blister inserted into the blister support member at an angle through the slot.

33. An inhaler according to claim 32, wherein the longitudinal axis of the chamber is substantially at right-angles to the direction of insertion of a blister into the blister support member, when the housing is in its lowered blister pierced position.

34. An inhaler according to claim 31, wherein the blister support member is configured so as to support a blister such that the plane of a blister surrounding the blister bowl lies at an acute angle relative to the longitudinal axis of the chamber when the housing is in its home position prior to pivotal movement of the housing to lower it onto the blister support member to pierce said blister.

35. An inhaler according to claim 34, wherein the longitudinal axis of the chamber lies substantially at right-angles to the plane of a lid of a blister after the housing has been pivoted out of its home position into its lowered position to pierce said blister.

36. An inhaler according to claim 20, wherein the blister support member has a lower supporting surface to stand the blister support member, together with the housing, upright on a level surface when not in use.

37. An inhaler according to claim 36, wherein the longitudinal axis of the chamber lies substantially at right-angles to the plane of the lower supporting surface when the housing is in a first position prior to pivotal movement of the housing relative to the blister support member to pierce said blister.

38. An inhaler according to claim 21, wherein the blister seat comprises a blister support surface to support the periphery of a blister surrounding a blister bowl.

39. An inhaler according to claim 38, wherein the blister support surface is located below a surrounding wall such that the edges of a blister located on the support surface are supported between the support surface and the surrounding wall.

40. An inhaler according to claim 38, wherein the blister support surface has a generally U-shaped cut out to receive a blister bowl and an arcuately shaped cantilever arm extends into the cut out from the base of the U- shape.

41. An inhaler according to claim 40, wherein the cantilever has an enlarged head with a blister bowl engaging lip, the cantilever arm resiliently deforming to allow a blister bowl to ride over the head and locate within the arcuately shaped cantilever arm to retain the blister within the device.

42. An inhaler according to claim 20, wherein the blister support member has a tab receiving recess formed in a side wall of the blister support member to receive a folded blister tab of a pre-loaded blister.

43. An inhaler according to claim 31, wherein the blister support member has convex shaped support surfaces that cooperate with corresponding concave shaped support surfaces on the housing when the housing is rotated relative to the blister support member.

44. An inhaler according to claim 43, wherein the slot is formed in a depression in the blister support member so that a blister tab extending from the slot does not protrude beyond the walls of the device.

45. An inhaler according to claim 1, comprising a cap positionable such that it substantially covers the housing and the blister support member after a blister has been inserted into the slot and whilst the housing is in its first position, the cap being positionable without interfering with a blister tab extending from said slot.

46. An inhaler according to claim 45, wherein an opening is formed between the housing and the blister support member to enable a user to see the blister piercing element and a blister inserted into the slot in the blister support member.

47. An inhaler according to claim 1, comprising a dose containing blister having a tab such that, when the blister is inserted into the slot, the tab protrudes from the slot and facilitates the removal of the blister from the slot after inhalation.

48. An inhaler according to claim 47, wherein the tab is foldable relative to the remaining portion of the blister received in the slot such that the tab substantially flush against the base when the blister is received in the slot.

49. An inhaler according to claim 48, wherein the base comprises a recess to locate a folded tab therein.

50. An inhaler according to claim 48, wherein the base and the cap are configured so that the cap extends over and covers the folded tab.

51. An inhaler according to claim 1, wherein the blister support member comprises a seat to support a blister that has been inserted through the slot in its first position.

52. An inhaler comprising a housing having a mouthpiece through which a user may inhale a dose of medicament and a blister support member having a slot to receive a dose containing blister, the housing and the blister support member being pivotable relative to each other between a first position for insertion of a blister into said slot and, a second, pierced position, in which a blister piercing element carried by the housing pierces an inserted blister so that when a user inhales on the mouthpiece, the dose is entrained in an airflow and flows out of the blister through the mouthpiece and into the user's airway, wherein the housing comprises a substantially cylindrical chamber having an inlet at one end for the flow of drug laden air into the chamber from a pierced blister and an outlet at its opposite end for the flow of drug laden air out of the mouthpiece and into a patient's airway and wherein the blister support member is pivotally mounted within, and extends from, the housing to enable a user to pivot the blister support member relative to the housing into said second, pierced position so that a blister inserted into the slot and supported by the blister support member is pierced by said blister piercing element and the blister support member includes a lever portion that extends into a cut-out section formed in a wall of the housing and fills only a portion of the cut-out section in the wall of the housing such that the housing and the lever portion together define a recess therebetween, with the slot is located such that a blister tab of a blister received in the blister support member protrudes from said slot into said recess.

53. An inhaler according to claim 52, wherein the slot is configured such that a blister tab extending into said recess is spaced from the housing and from the blister support member when the blister support member is in its first position.

54. An inhaler according to claim 53, wherein the blister support member and the housing is configured such that, when the blister support member is rotated into its second, pierced position, a blister tab protruding from the aperture into the recess is in a less accessible position than when the blister support member is in its first position.

55. An inhaler according to claim 52, comprising a cap positionable such that it substantially covers the housing and the blister support member after a blister has been inserted into the slot and whilst the housing is in its first position, the cap being positionable without interfering with a blister tab extending from said slot.

56. An inhaler according to claim 55, wherein an opening is formed between the housing and the blister support member to enable a user to see the blister piercing element and a blister inserted into the slot in the blister support member.

57. An inhaler comprising a housing having a mouthpiece through which a user may inhale a dose of medicament and a blister support member having a slot to receive a dose containing blister, the housing and the blister support member being pivotable relative to each other between a first position for insertion of a blister into said slot and, a second, pierced position, in which a blister piercing element carried by the housing pierces an inserted blister so that when a user inhales on the mouthpiece, the dose is entrained in an airflow and flows out of the blister through the mouthpiece and into the user's airway, wherein the housing comprises a substantially cylindrical chamber having an inlet at one end for the flow of drug laden air into the chamber from a pierced blister and an outlet at its opposite end for the flow of drug laden air out of the mouthpiece and into a patient's airway, wherein the blister support member comprises a seat to support a blister that has been inserted through the slot in its first position.

58. An inhaler according to claim 57, wherein the blister seat comprises a blister support surface to support the periphery of a blister surrounding a blister bowl.

59. An inhaler according to claim 58, wherein the blister support surface is located below a surrounding wall such that the edges of a blister located on the support surface are supported between the support surface and the surrounding wall.

60. An inhaler according to claim 58, wherein the blister support surface has a generally U-shaped cut out to receive a blister bowl and an arcuately shaped cantilever arm extends into the cut out from the base of the U- shape.

61. An inhaler according to claim 60, wherein the cantilever has an enlarged head with a blister bowl engaging lip, the cantilever arm resiliently deforming to allow a blister bowl to ride over the head and locate within the arcuately shaped cantilever arm to retain the blister within the device.

* * * * *